US010638918B2

(12) United States Patent
Atarot et al.

(10) Patent No.: US 10,638,918 B2
(45) Date of Patent: May 5, 2020

(54) MANUAL CONTROL SYSTEM FOR MANEUVERING AN ENDOSCOPE

(71) Applicant: TransEnterix Europe S.a.r.l., Lugano (TI) (CH)

(72) Inventors: Gal Atarot, Kfar Saba (IL); Mordehai Sholev, Amikam (IL)

(73) Assignee: TransEnterix Europe S.a.r.l., Lugano (TI) (CH)

(*) Notice: Subject to any disclaimer, the term of this patent is extended or adjusted under 35 U.S.C. 154(b) by 553 days.

(21) Appl. No.: 14/380,082

(22) PCT Filed: Feb. 28, 2013

(86) PCT No.: PCT/IL2013/050183
§ 371 (c)(1),
(2) Date: Aug. 21, 2014

(87) PCT Pub. No.: WO2013/128457
PCT Pub. Date: Sep. 6, 2013

(65) Prior Publication Data
US 2015/0031953 A1 Jan. 29, 2015

Related U.S. Application Data

(60) Provisional application No. 61/604,535, filed on Feb. 29, 2012.

(51) Int. Cl.
*A61B 1/00* (2006.01)
*A61B 1/005* (2006.01)
(Continued)

(52) U.S. Cl.
CPC .......... *A61B 1/0016* (2013.01); *A61B 1/0051* (2013.01); *A61B 1/00133* (2013.01);
(Continued)

(58) Field of Classification Search
CPC ............ A61B 1/00131; A61B 1/00133; A61B 1/00147; A61B 1/00149; A61B 1/0016;
(Continued)

(56) References Cited

U.S. PATENT DOCUMENTS 5,553,198 A 9/1996 Wang et al.
8,058,969 B1 11/2011 Lai et al.
(Continued)

FOREIGN PATENT DOCUMENTS

AU 2007234510 A1 6/2007
JP 06063003 A 3/1994

OTHER PUBLICATIONS

Atarot et al., Manual Control System for Maneuvering an Endoscope, co-pending U.S. Appl. No. 14/380,082, filed Aug. 21, 2014, 118 pages.
(Continued)

*Primary Examiner* — Ryan N Henderson

(57) ABSTRACT

The present invention provides a system for maneuvering an endoscope (SFME) during a medical procedure, comprising a. at least one maneuvering system, adapted to maneuver said endoscope in at least two degrees of freedom (DOF); and, b. at least one joystick unit in communication with said maneuvering system, adapted to operate said maneuvering system; wherein operation of said joystick results in movement of said endoscope by means of said maneuvering system.

13 Claims, 24 Drawing Sheets

(51) Int. Cl.
*A61B 34/30* (2016.01)
*A61B 34/35* (2016.01)
*A61B 34/00* (2016.01)

(52) U.S. Cl.
CPC .......... *A61B 1/00147* (2013.01); *A61B 34/30* (2016.02); *A61B 34/35* (2016.02); *A61B 34/70* (2016.02); *A61B 34/74* (2016.02); *A61B 2034/301* (2016.02); *A61B 2034/302* (2016.02); *A61B 2034/742* (2016.02)

(58) Field of Classification Search
CPC ......... A61B 34/20; A61B 34/30; A61B 34/32; A61B 34/34; A61B 34/37; A61B 34/70; A61B 34/71; A61B 34/72; A61B 34/74; A61B 34/75; A61B 34/76; A61B 34/77; A61B 2034/301; A61B 2034/302; A61B 2034/303; A61B 2034/304; A61B 2034/741; A61B 2034/742; A61B 2034/743; A61B 2034/744
See application file for complete search history.

(56) References Cited

U.S. PATENT DOCUMENTS

| 2002/0032452 | A1* | 3/2002 | Tierney ............... G06Q 30/02 606/130 |
|---|---|---|---|
| 2003/0195389 | A1 | 10/2003 | Motoki et al. |
| 2004/0239631 | A1 | 12/2004 | Gresham |
| 2005/0119527 | A1 | 6/2005 | Banik et al. |
| 2006/0100501 | A1 | 5/2006 | Berkelman et al. |
| 2007/0142824 | A1 | 6/2007 | Devengenzo et al. |
| 2009/0312101 | A1 | 12/2009 | Pope |
| 2010/0262162 | A1* | 10/2010 | Omori ................ A61B 1/00149 606/130 |
| 2011/0118748 | A1 | 5/2011 | Itkowitz |
| 2011/0144659 | A1 | 6/2011 | Sholev |
| 2011/0175989 | A1 | 7/2011 | Islam |
| 2012/0041263 | A1 | 2/2012 | Sholev |
| 2012/0071752 | A1* | 3/2012 | Sewell ..................... A61B 6/12 600/424 |
| 2013/0123804 | A1 | 5/2013 | Sholev et al. |
| 2014/0163359 | A1 | 6/2014 | Sholev et al. |
| 2014/0194896 | A1 | 7/2014 | Frimer et al. |
| 2014/0221738 | A1 | 8/2014 | Sholev et al. |
| 2014/0228632 | A1 | 8/2014 | Sholev et al. |

OTHER PUBLICATIONS

Atarot et al., Overall Endoscopic Control System, co-pending U.S. Appl. No. 14/380,086, filed Sep. 16, 2014, 79 pages.
International Search Report dated Jun. 28, 2013 in corresponding International Application No. PCT/IL2013/050183.

* cited by examiner

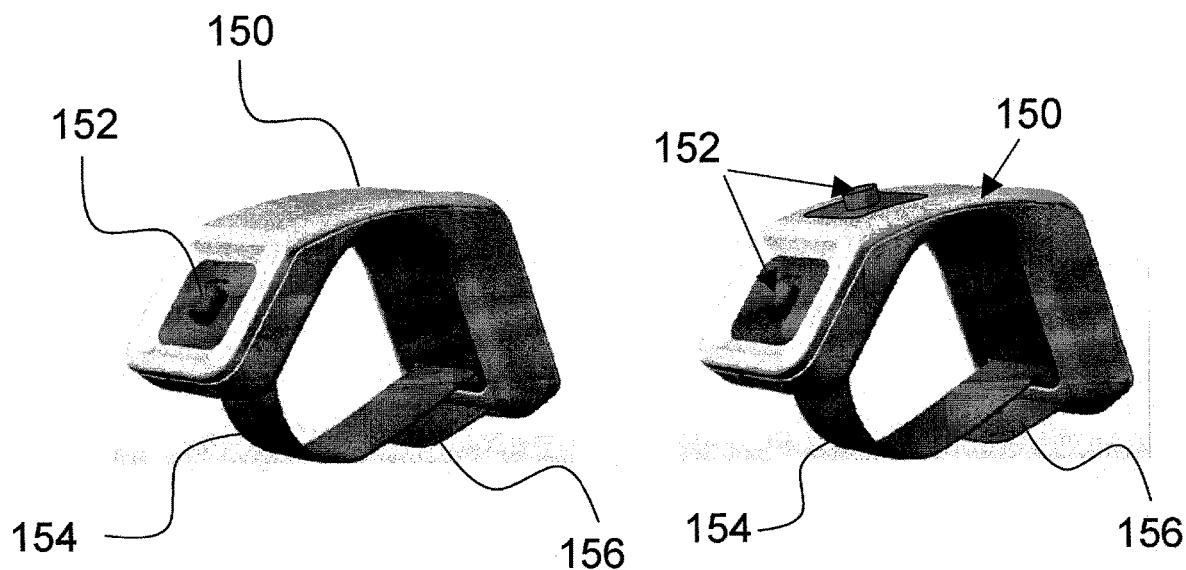
Fig. 2a
Fig. 2b
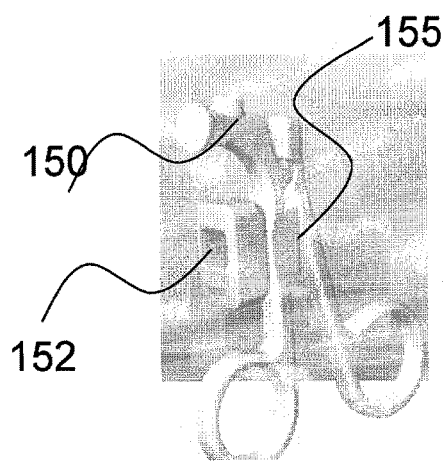
Fig. 2c
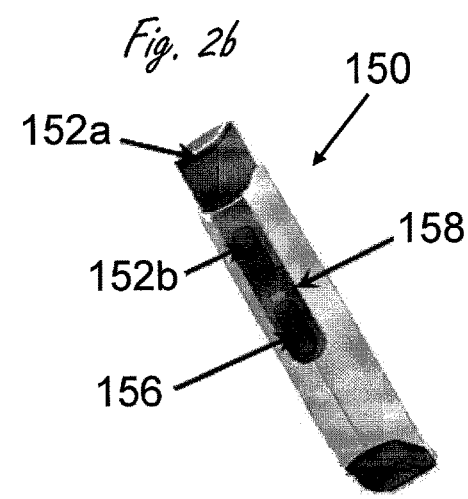
Fig. 2d

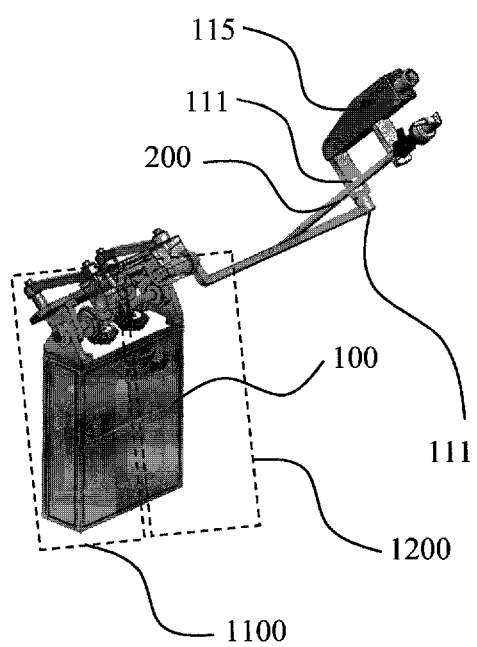
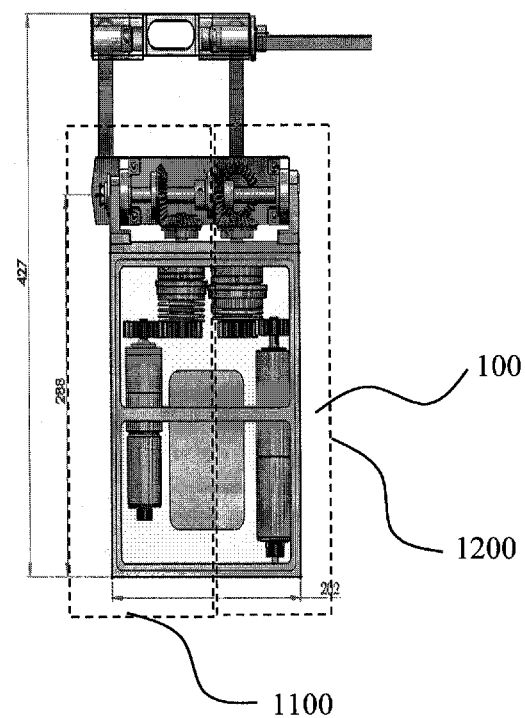
Fig. 12a
Fig. 12b

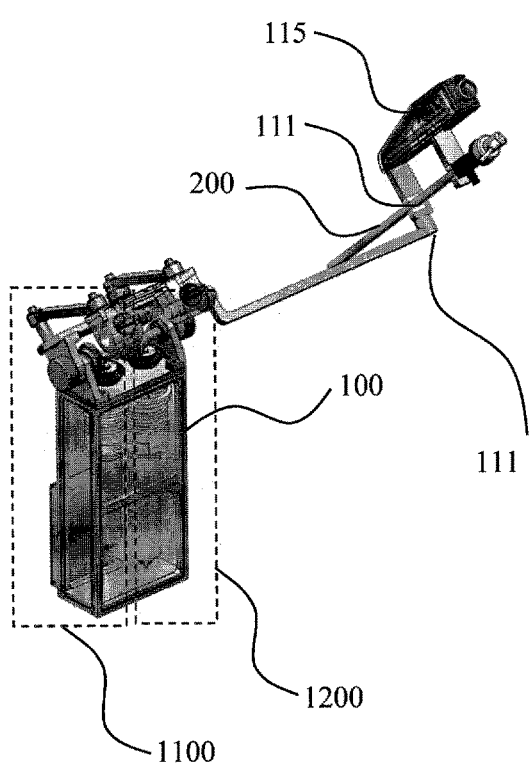
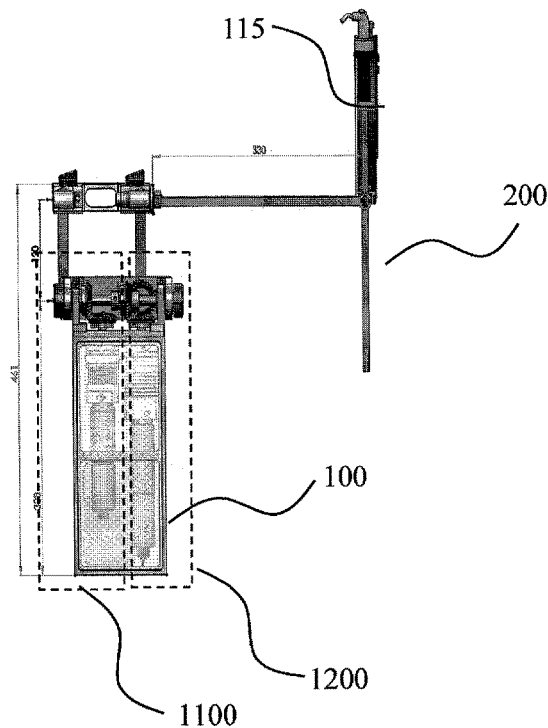
Fig. 13a
Fig. 13b

MANUAL CONTROL SYSTEM FOR MANEUVERING AN ENDOSCOPE

FIELD OF THE INVENTION

The present invention generally relates to means and methods for simply maneuvering an endoscope by an endoscope user. Moreover, this present invention discloses a compact configuration of devices used for different manual actions upon the endoscope.

BACKGROUND OF THE INVENTION

Laparoscopic surgery is becoming increasingly popular with patients because the scars are smaller and the period of recovery is shorter. Laparoscopic surgery requires special training of the surgeon or gynecologist and the theatre nursing staff. The equipment is often expensive and is not available in all hospitals. During laparoscopic surgery, it is often required to shift the spatial placement of the endoscope in order to present the surgeon with an optimal view. Conventional laparoscopic surgery makes use of either human assistants that manually shift the instrumentation or, alternatively, robotic automated assistants (such as JP patent No. 06063003).

In laparoscopic surgery, the surgeon performs the operation through small holes using long instruments and observing the internal anatomy with an endoscope camera. The endoscope is conventionally held by a camera assistant since the surgeon must perform the operation using both hands. The surgeon's performance is largely dependent on the camera position relative to the instruments and on a stable image shown at the monitor; also the picture shown must be in the right orientation. The main problem is that it is difficult both for the assistant to keep the endoscope in the right spatial position, and for the assistant to hold the endoscope steadily, keeping the scene in the right orientation. To overcome these problems, several new technologies have been developed, using robots to hold the endoscope while the surgeon performs the procedure, e.g., Lapman, Endoassist etc. But these technologies are expensive, difficult to install, uncomfortable to use, limit the dexterity of the surgeon and have physical dimensions much larger that all the other operating tools. Relative to the required action, they also require a large region to be kept free for their movement and have several arms, moving around different axes. Another robot, LER (which was developed by the TIMC-GMCAO Laboratory), US. patent application Ser. No. 200/6100501 consists of a compact camera-holder robot that rests directly on the patient's abdomen and an electronic box containing the electricity supply and robot controllers. LER has relatively small dimensions but has a 110 mm diameter base ring that must be attached to, or be very close to, the patient's skin. This ring occupies a place over the patient's body, thus limiting the surgeon's activities: other trochars can not be placed there, whether or not the surgeon would prefer this, possibly changing the surgeon's usual method of carrying our the procedure, and sometimes forcing the setup process to be as long as 40 minutes. Also, the LER has only 3 degrees of freedom and is unable to control the orientation of the picture shown to surgeon (the LER cannot rotate the endoscope around its longitudinal axis).

However, even the improved technologies still limit the dexterity of the surgeon and fail to provide the necessary four degrees of freedom. Another disadvantage of these technologies is that they lack the ability to control fully both the spatial position of the endoscope tube and its orientation during the laparoscopic surgery, so that the surgeon may view any desired area within the working envelope in the body being operated on.

Therefore, there is still a long felt need for a camera holder that will hold the endoscope steady and that will allow full control of the endoscope in all four degrees of freedom, without limiting the dexterity of the surgeon. Furthermore, there is also a long felt need for a camera holder that will provide the ability to control the spatial orientation of an endoscope tube, so that the surgeon may reach any desired area within the working envelope in operated body and may view that area from any desired angle.

SUMMARY OF THE INVENTION

An object of the invention is to disclose a system for maneuvering an endoscope (SFME) during a medical procedure comprising (a) at least one maneuvering system unit, adapted to maneuver the endoscope in at least two degrees of freedom (DOF); and (b) at least one joystick unit in communication with the maneuvering system unit, adapted to operate the maneuvering system unit; wherein operation of said joystick unit results in movement of said endoscope by means of said maneuvering system.

It is another object of the invention to disclose the system as defined above, wherein the joystick unit is wearable by a user of the system.

It is another object of the invention to disclose the system as defined above, wherein the joystick unit is coupled to at least one surgical tool used in the medical procedure.

It is another object of the invention to disclose the system as defined above, wherein the at least one surgical tool is an endoscope.

It is another object of the invention to disclose the system as defined above, wherein the movement of the joystick is proportional to the movement of the endoscope.

It is another object of the invention to disclose the system as defined above, wherein the joystick unit is a force joystick.

It is another object of the invention to disclose the system as defined above, wherein the joystick unit comprises a base and lever coupled to the base, such that movement of the lever results in movement of the endoscope; further wherein the movement of the lever is proportional to the movement of the endoscope.

It is another object of the invention to disclose the system as defined above, wherein the joystick unit comprises a base and a button jointly connected to the base, such that movement of the button results in movement of the endoscope; further wherein the movement of the button is proportional to the movement of the endoscope.

It is another object of the invention to disclose the system as defined above, wherein the joystick unit comprises a touchscreen, such that a touch and a movement on the touchscreen results in movement of the endoscope; further wherein the touch and movement on the touchscreen is proportional to the movement of the endoscope.

It is another object of the invention to disclose the system as defined above, wherein the joystick unit comprises at least one sound sensor, adapted to sense predetermined sound patterns; the joystick unit adapted to operate the maneuvering system based on the predetermined sound patterns.

It is another object of the invention to disclose the system as defined above, wherein the SFME additionally comprises means adapted to restrain the velocity of the endoscope, such that when the means are activated, the velocity of the endoscope is restrained.

It is another object of the invention to disclose the system as defined above, wherein the joystick unit additionally comprises n sensors, where n is an integer larger than one.

It is another object of the invention to disclose the system as defined above, wherein the sensors are selected from a group consisting of a motion sensor, a heat sensor, an electric sensor, a sound sensor, a pressure sensor, an optical sensor and any combination thereof.

It is another object of the invention to disclose the system as defined above, wherein at least one of the n sensors is activated in case of power failure.

It is another object of the invention to disclose the system as defined above, wherein at least one of the n sensors is activated when the system is connected to power.

It is another object of the invention to disclose the system as defined above, wherein the joystick unit is characterized by an external surface.

It is another object of the invention to disclose the system as defined above, wherein the at least one motion sensor detects motion upon the external surface of the joystick unit.

It is another object of the invention to disclose the system as defined above, wherein the at least one motion sensor detects motion perpendicular to the external surface of the joystick unit.

It is another object of the invention to disclose the system as defined above, wherein, if the joystick unit's speed of motion is above a predetermined value, the endoscope's speed is at a predetermined value.

It is another object of the invention to disclose the system as defined above, wherein the at least one heat sensor is adapted to sense temperature in the range of about 35 to about 42 degrees.

It is another object of the invention to disclose the system as defined above, wherein the system is adapted to enable maneuvering of the endoscope at such times as the at least one heat sensor senses temperatures in the range of about 35 to about 42 degrees.

It is another object of the invention to disclose the system as defined above, wherein the at least one heat sensor is adapted to provide a thermal image, and where the at least one heat sensor is coupled to a processing unit adapted to provide the endoscope user with the thermal image.

It is another object of the invention to disclose the system as defined above, wherein the system is adapted to enable maneuvering of the endoscope at such times as analysis of the image by the processing system detects a human hand; further wherein the system is adapted to prevent maneuvering of the endoscope at such times when the analysis of the image by the processing unit fails to detect an image of a human hand.

It is another object of the invention to disclose the system as defined above, wherein at least one electric sensor is adapted to sense power failure.

It is another object of the invention to disclose the system as defined above, wherein at least one electric sensor is adapted to sense electric conductivity of a subject's body.

It is another object of the invention to disclose the system as defined above, wherein the system is adapted to enable maneuvering of the endoscope at such times when the sensor senses the conductivity of the subject's body; further wherein the system is adapted to prevent maneuvering of the endoscope at such times as the sensor fails to sense the conductivity of the subject's body.

It is another object of the invention to disclose the system as defined above, wherein at least one sound sensor is adapted to sense predetermined sound patterns.

It is another object of the invention to disclose the system as defined above, wherein the endoscope is maneuverable according to the at least one predetermined sound pattern sensed by the at least one sound sensor.

It is another object of the invention to disclose the system as defined above, wherein at least one pressure sensor is adapted to sense pressure applied to the joystick unit.

It is another object of the invention to disclose the system as defined above, wherein the pressure sensed by at least one pressure sensor affects the SFME in a manner selected from a group consisting of: when the pressure sensed by the at least one pressure sensor is above a predetermined threshold, the SFME is activated, when the pressure sensed by the at least one pressure sensor is above a predetermined threshold, the SFME is de-activated, and when the pressure sensed by the at least one pressure sensor is below a predetermined threshold, the SFME is de-activated.

It is another object of the invention to disclose the system as defined above, wherein at least one optical sensor is adapted to sense visual changes according to at least one predetermined visual pattern.

It is another object of the invention to disclose the system as defined above, wherein the endoscope is maneuverable according to at least one predetermined visual pattern.

It is another object of the invention to disclose the system as defined above, additionally comprising an interface system adapted to enable communication between the joystick unit and the maneuvering system unit.

It is another object of the invention to disclose the system as defined above, wherein the communication means comprises a member selected from a group consisting of a wired communication means, a wireless communication means and any combination thereof.

It is another object of the invention to disclose the system as defined above, wherein the SFME comprises at least one second joystick unit adapted to zoom the endoscope by means of the maneuvering system unit.

It is another object of the invention to disclose the system as defined above, wherein the second joystick unit is wearable by a system user.

It is another object of the invention to disclose the system as defined above, wherein the second joystick unit is coupled to at least one surgical tool.

It is another object of the invention to disclose the system as defined above, wherein the at least one surgical tool is an endoscope.

It is another object of the invention to disclose the system as defined above, wherein the at least one joystick unit is adapted to control and to direct the endoscope via the maneuvering system on a surgical tool.

It is another object of the invention to disclose the system as defined above, wherein selection of the at least one surgical tool is obtained by activating the at least one joystick unit; further wherein the activation of the at least one joystick unit is obtained by depression of the joystick unit, voice activating the same, prolonged depression on the same, double clicking on the same and any combination thereof.

It is another object of the invention to disclose the system as defined above, additionally comprising
(a) at least one wearable operator comprising at least one wireless transmitter, adapted to transmit a signal once the at least one wearable operator is activated; the at least one wearable operator is either wire or wirelessly in communication with at least one surgical instrument;

(b) at least one wireless receiver; adapted to receive the signal sent by the transmitter;

(c) at least one laparoscopy computerized system, in communication with the wireless receiver, adapted to provide a visual onscreen depiction of the at least one instrument to be selected following the activation of the at least one wearable operator; and, (d) at least one video screen; wherein the system is adapted to control and to direct the endoscope via the laparoscopy computerized system and the maneuvering system on the instrument to be selected following the activation of the at least one wearable operator.

It is another object of the invention to disclose the system as defined above, wherein the communication between the at least one of the wearable operators and the instrument is either wire or wirelessly coupling.

It is another object of the invention to disclose the system as defined above, wherein the wearable operator is worn by the surgeon on a predetermined body part.

It is another object of the invention to disclose the system as defined above, wherein the predetermined body part is selected from a group consisting of: the hand of the surgeon, at least one of the fingers of the surgeon, the thigh of the surgeon, the neck of the surgeon, at least one of the legs of the surgeon, the knee of the surgeon, the head of the surgeon and any combination thereof.

It is another object of the invention to disclose the system as defined above, wherein the shape of the wearable operator is selected from a group consisting of a ring, a bracelet and any combination thereof.

It is another object of the invention to disclose the system as defined above, wherein the wearable operator is coupled to a predetermined location on the instrument by means of an adaptor.

It is another object of the invention to disclose the system as defined above, wherein the wearable operator is adjustable so as to fit the predetermined location of the different instruments, each of which is characterized by a different size and shape.

It is another object of the invention to disclose the system as defined above, wherein the wearable operator comprises a body having at least two portions at least partially overlapping each other; the two portions are adapted to grasp and hold either the instrument or the predetermined body part there-between, such that a tight-fit coupling between the two portions and the instrument or the predetermined body part is obtained.

It is another object of the invention to disclose the system as defined above, wherein one of the two portions is rotationally movable relative to the other, such that when the wearable operator is coupled to the instrument, fine-tuned movement of the two body portions is obtainable so as to provide the tight-fit coupling between the two portions and the instrument or the predetermined body part.

It is another object of the invention to disclose the system as defined above, wherein the two portions are rotationally movable relative to each other, such that when the wearable operator is coupled to the instrument, fine-tuned movement of the two body portions is obtainable so as to provide the tight-fit coupling between the two portions and the instrument or the predetermined body part.

It is another object of the invention to disclose the system as defined above, wherein the wearable operator comprises (a) at least one flexible and stretchable strip; and (b) loop-closing means adapted to close a loop with the at least one flexible and stretchable strip; the at least one flexible and stretchable strip and the loop-closing means are provided so as to fit the wearable operator to at least one selected from a group consisting of (a) the predetermined location of the different instruments; (b) the predetermined body part of the surgeon, each of which is characterized by a different size and shape.

It is another object of the invention to disclose the system as defined above, wherein the flexible and stretchable strip is made of material selected from a group consisting of silicone, rubber and any combination thereof.

It is another object of the invention to disclose the system as defined above, wherein the wireless transmitter is adapted to locate the position of at least one of the instruments.

It is another object of the invention to disclose the system as defined above, wherein selection of the at least one instrument is obtained by activating the at least one wearable operator; further wherein the activation of the at least one wearable operator is obtained by depression on a predetermined location in the wearable operator, voice activating the same, prolonged depression on the same, double clicking on the same and any combination thereof.

It is another object of the invention to disclose the system as defined above, wherein the laparoscopy computerized system directs the endoscope by using image information shown on the video screen without the help of assistants.

It is another object of the invention to disclose the system as defined above, wherein the conventional laparoscopy computerized system comprises at least one surgical instrument spatial location software, adapted to locate the 3D spatial position of the at least one instrument; further wherein the conventional laparoscopy computerized system comprises at least one automated assistant maneuvering system; the automated assistant maneuvering system is coupled to the endoscope and is adapted to direct the endoscope to the at least one instrument, the instrument selected following the activation of the at least one wearable operator.

It is another object of the invention to disclose the system as defined above, wherein each transmitted signal from the wearable operator and the wireless transmitter is matched to at least one of the instruments.

It is another object of the invention to disclose the system as defined above, wherein the at least one joystick unit is adapted to control and to direct the endoscope via the maneuvering system on the surgical instrument to which the activated wearable operator is coupled.

It is another object of the invention to disclose the system as defined above, wherein selection of the at least one instrument is obtained by activating the at least one joystick unit; further wherein the activation of the at least one joystick unit is obtained by depression of the joystick unit, voice activating the same, prolonged depression on the same, double clicking on the same and any combination thereof.

It is another object of the invention to disclose the system as defined above, wherein said at least one joystick unit is adapted to control and to direct said endoscope via said maneuvering system on a surgical tool.

It is another object of the invention to disclose the system as defined above, wherein selection of said at least one surgical tool is obtained by activating said at least one joystick unit; further wherein the activation of said at least one joystick unit is obtained by depression of said joystick unit, voice activating the same, prolonged depression on the same, double clicking on the same and any combination thereof.

It is another object of the invention to disclose the system as defined above, additionally comprising (a) at least one wearable operator comprising at least one wireless transmitter, adapted to transmit a signal once said at least one wearable operator is activated; said at least one wearable operator is either wire or wirelessly in communication with at least one surgical instrument; (b) at least one wireless receiver; adapted to receive said signal sent by said transmitter; (c) at least one laparoscopy computerized system, in communication with said wireless receiver, adapted to provide a visual onscreen depiction of said at least one instrument to be selected following the activation of said at least one wearable operator; and, (d) at least one video screen; wherein said system is adapted to control and to direct said endoscope via said laparoscopy computerized system and said maneuvering system on said instrument to be selected following the activation of said at least one wearable operator.

It is another object of the invention to disclose the system as defined above, wherein said communication between said at least one of said wearable operators and said instrument is either wire or wirelessly coupling.

It is another object of the invention to disclose the system as defined above, wherein said wearable operator is worn by said surgeon on a predetermined body part.

It is another object of the invention to disclose the system as defined above, wherein said predetermined body part is selected from a group consisting of: the hand of said surgeon, at least one of the fingers of said surgeon, the thigh of said surgeon, the neck of said surgeon, at least one of the legs of said surgeon, the knee of said surgeon, the head of said surgeon and any combination thereof.

It is another object of the invention to disclose the system as defined above, wherein the shape of said wearable operator is selected from a group consisting of a ring, a bracelet and any combination thereof.

It is another object of the invention to disclose the system as defined above, wherein said wearable operator is coupled to a predetermined location on said instrument by means of an adaptor.

It is another object of the invention to disclose the system as defined above, wherein said wearable operator is adjustable so as to fit said predetermined location of said different instruments, each of which is characterized by a different size and shape.

It is another object of the invention to disclose the system as defined above, wherein said wearable operator comprises a body having at least two portions at least partially overlapping each other; said two portions are adapted to grasp and hold either said instrument or said predetermined body part there-between, such that a tight-fit coupling between said two portions and said instrument or said predetermined body part is obtained.

It is another object of the invention to disclose the system as defined above, wherein one of said two portions is rotationally movable relative to the other, such that when said wearable operator is coupled to said instrument, fine-tuned movement of said two body portions is obtainable so as to provide said tight-fit coupling between said two portions and said instrument or said predetermined body part.

It is another object of the invention to disclose the system as defined above, wherein said two portions are rotationally movable relative to each other, such that when said wearable operator is coupled to said instrument, fine-tuned movement of said two body portions is obtainable so as to provide said tight-fit coupling between said two portions and said instrument or said predetermined body part.

It is another object of the invention to disclose the system as defined above, wherein said wearable operator comprises (a) at least one flexible and stretchable strip; and (b) loop-closing means adapted to close a loop with said at least one flexible and stretchable strip; said at least one flexible and stretchable strip and said loop-closing means are provided so as to fit said wearable operator to at least one selected from a group consisting of (a) said predetermined location of said different instruments; (b) said predetermined body part of said surgeon, each of It is another object of the invention to disclose the system as defined above, which is characterized by a different size and shape.

It is another object of the invention to disclose the system as defined above, wherein said flexible and stretchable strip is made of material selected from a group consisting of silicone, rubber and any combination thereof.

wherein said wireless transmitter is adapted to locate the position of at least one of said instruments.

It is another object of the invention to disclose the system as defined above, wherein selection of said at least one instrument is obtained by activating said at least one wearable operator; further wherein the activation of said at least one wearable operator is obtained by depression on a predetermined location in said wearable operator, voice activating the same, prolonged depression on the same, double clicking on the same and any combination thereof.

It is another object of the invention to disclose the system as defined above, wherein said laparoscopy computerized system directs said endoscope by using image information shown on said video screen without said help of assistants.

It is another object of the invention to disclose the system as defined above, wherein said conventional laparoscopy computerized system comprises at least one surgical instrument spatial location software, adapted to locate the 3D spatial position of said at least one instrument; further wherein said conventional laparoscopy computerized system comprises at least one automated assistant maneuvering system; said automated assistant maneuvering system is coupled to said endoscope and is adapted to direct said endoscope to said at least one instrument, said instrument selected following the activation of said at least one wearable operator.

It is another object of the invention to disclose the system as defined above, wherein each transmitted signal from said wearable operator and said wireless transmitter is matched to at least one of said instruments.

It is another object of the invention to disclose the system as defined above, wherein a single device comprises the joystick unit and the second joystick unit.

It is another object of the invention is to disclose the system as defined above, additionally comprising:

1. a first mechanism, comprising:
    a. at least one first coaxial transmission means 101; the first coaxial transmission means 101 defines a first plane and is characterized by a first axis of rotation which is substantially orthogonal to the first plane;
    b. at least one second coaxial transmission means 102; the second coaxial transmission means 102 defines a second plane and is characterized by a second axis of rotation; the second axis of rotation is substantially orthogonal to the second plane; additionally, it is rotatably connected to the first coaxial transmission means 101; where the second plane is substantially orthogonal to the first plane; and c. at least one first means 106 adapted to rotate the first coaxial transmission means 101 around the first axis of rotation;

where the first coaxial transmission means transmits rotation to the second coaxial transmission means 102; and, 2. a second mechanism, comprising:

a. at least one third coaxial transmission means 103 which defines a third plane and is characterized by a third axis of rotation; the third axis of rotation is substantially orthogonal to the third plane;

b. at least one fourth coaxial transmission means 104 which defines a fourth plane and is characterized by a fourth axis of rotation, the fourth axis of rotation is substantially orthogonal to the fourth plane; and is rotatably connected to the third coaxial transmission means 103; where fourth plane is substantially orthogonal to the third plane;

c. at least one fifth coaxial transmission means 105 which defines a fifth plane and a fifth axis of rotation; the fifth axis of rotation is substantially orthogonal to the fifth plane; fifth coaxial transmission means 105 is rotatably connected to the fourth coaxial transmission means 104 and is substantially orthogonal to the fourth plane;

d. at least one second means adapted to rotate the third coaxial transmission means 103 around the third axis of rotation;

where the third coaxial transmission means 103 transmits rotation to the fourth coaxial transmission means 104; the fourth coaxial transmission means 104 transmit rotation to the fifth coaxial transmission means 105;

wherein the first mechanism and the second mechanism are adapted to rotate the endoscope around at least one second axis of rotation being substantially orthogonal to the second plane; and around at least one fifth axis of rotation being substantially orthogonal to the fifth plane, such that the second axis of rotation and the fifth axis of rotation are positioned at an angle A relative to each other.

It is another object of the invention to disclose the system as defined above, wherein A is in the range of about 0 degrees to about 180 degrees.

It is another object of the invention to disclose the system as defined above, additionally comprising at least one pivoting support 111 pivotally attached to the endoscope; the pivoting support adapted to enable the endoscope to pivot around the pivoting support.

It is another object of the invention to disclose the system as defined above, wherein the pivoting support is a gimbal.

It is another object of the invention to disclose the system as defined above, additionally comprising at least one third mechanism in communication with the first mechanism and the second mechanism, the third mechanism comprising (i) at least one pivoting support adapted to be pivotally attached to the endoscope; the pivoting support adapted to enable the endoscope 200 to pivot around the pivoting support; and (ii) at least one joint 114 the joint mechanically connected to the pivoting support 111, thereby enabling the endoscope 200 to rotate freely in two orthogonal axes around an insertion point;

the endoscope pivotally attached to the joint and the pivoting support can pivot at the insertion point independent of the distance between the pivoting support, the joint, and the insertion point;

where the third mechanism is coupled at its distal end to the endoscope 200 and at its proximal end the same is coupled to at least one mechanism selected from a group consisting of the first mechanism, the second mechanism and any combination thereof;

wherein the second joint is located at a predetermined distance from the first joint.

It is another object of the invention to disclose the system as defined above, wherein the pivoting support comprises a gimbal.

It is another object of the invention to disclose the system as defined above, wherein the joint comprises a gimbal.

It is another object of the invention to disclose the system as defined above, additionally comprising at least one zoom mechanism, adapted to maneuver the endoscope along the main longitudinal axis of the same.

It is another object of the invention to disclose the system, wherein the zoom mechanism comprises clasping means adapted to enable reversible reciprocating movement along the main longitudinal axis of the endoscope 200.

It is another object of the invention to disclose the system as defined above, wherein the zoom mechanism is operable by at least one motor.

It is another object of the invention to disclose the system as defined above, where the third mechanism comprises a plurality of q joints, at least one of which is coupled to the pivoting support, and at least one of which is coupled to the second mechanism; where q is an integer greater than or equal to one.

It is another object of the invention to disclose the system as defined above, wherein the first coaxial transmission means 101, the second coaxial transmission means 102, the third coaxial transmission means 103, the fourth coaxial transmission means 104, and the fifth coaxial transmission means 105 are selected from a group consisting of gearwheels, wheels, crown gears, bevel gears, spur gears, belts, and any combination thereof.

It is another object of the invention to disclose the system as defined above, wherein the system comprises attaching means adapted to reversibly couple the maneuvering system unit to a hospital bed.

It is another object of the invention to disclose the system as defined above, wherein the attaching means is selected from a group consisting of mechanical means, magnetic means and any combination thereof.

It is another object of the invention to disclose the system as defined above, wherein the mechanical attaching means is selected from a group consisting of a clip, a fastening element, non-adhesive tape, adhesive tape, a snap fastener, a button and any combination thereof.

It is another object of the invention to disclose the system as defined above, wherein the magnetic attaching means comprises at least one magnet, the magnet selected from a group consisting of a ferromagnet, a paramagnet and any combination thereof; where the magnetic means is attached to any selected from a group consisting of hospital bed, a maneuvering system unit, and any combination thereof.

It is another object of the invention to disclose the system as defined above, wherein the rotation of the SFME in the second plane of the SFME defines an angle $\theta$.

It is another object of the invention to disclose the system as defined above, wherein the angle $\theta$ varies between 0 and about 360 degrees, preferably between 0 and about 160 degrees.

It is another object of the invention to disclose the system as defined above, wherein rotation in the fifth plane of the SFME defines an angle $\psi$.

It is another object of the invention to disclose the system as defined above, wherein the angle ψ varies between 0 and about 360 degrees, preferably between 0 and 140 degrees.

It is another object of the invention to disclose the system as defined above, wherein the SFME enables control of rotation in angle ψ and angle θ.

It is another object of the invention to disclose the system as defined above, wherein movement of the joystick unit in any direction selected from a group consisting of ψ, θ and any combination thereof, enables control of movement of the endoscope in same direction as the movement of the joystick unit, the movement being proportional to one selected from a group consisting of the movement of the joystick unit, the speed of movement of the joystick unit, and any combination thereof.

It is another object of the invention to disclose the maneuvering system unit as defined above, additionally comprising a quick release handle adapted to disassemble the endoscope from the maneuvering system unit.

It is another object of the invention to disclose the system as defined above, wherein the first mechanism additionally comprises locking means adapted, upon power failure, to maintain in a predetermined orientation and to prevent any rotational movement of at least one selected from a group consisting of the first coaxial transmission means 101, the second coaxial transmission means 102 and any combination thereof.

It is another object of the invention to disclose the system as defined above, wherein the second mechanism additionally comprises locking means adapted, upon power failure, to maintain in a predetermined orientation and to prevent any rotational movement of at least one selected from a group consisting of the third coaxial transmission means 103, the fourth coaxial transmission means 104, the fifth coaxial transmission means 105, and any combination thereof.

It is another object of the invention to disclose the system as defined above, wherein the endoscope is adapted to acquire real-time images of a surgical environment within the subject's body.

It is another object of the invention to disclose a method for maneuvering an endoscope during a medical procedure, comprising steps of:
1. providing at least one endoscope;
2. providing a system for maneuvering an endoscope (SFME) during a medical procedure, the SFME comprising:
    a. at least one maneuvering system unit, adapted to maneuver the endoscope in at least two degrees of freedom (DOF); and
    b. at least one joystick unit in communication with the maneuvering system, adapted to operate the maneuvering system;
3. coupling the endoscope to maneuvering system unit;
4. maneuvering the joystick unit;
    thereby maneuvering the endoscope and controlling the movements of the same.

It is another object of the invention to disclose the method as defined above, additionally comprising a step of adapting the joystick unit to be worn by the system user.

It is another object of the invention to disclose the method as defined above, additionally comprising a step of coupling the joystick unit to at least one surgical tool used in a medical procedure.

It is another object of the invention to disclose the method as defined above, additionally comprising a step of selecting the surgical tool to be an endoscope.

It is another object of the invention to disclose the method as defined above, additionally comprising a step of adapting the SFME such that the movement of the joystick is proportional to the movement of the endoscope.

It is another object of the invention to disclose the method as defined above, additionally comprising a step of selecting the joystick unit to be a force joystick.

It is another object of the invention to disclose the method as defined above, additionally comprising a step of selecting the joystick unit such that the joystick unit comprises a base and lever coupled to the base, such that movement of the lever results in movement of the endoscope; further wherein the movement of the lever is proportional to the movement of the endoscope.

It is another object of the invention to disclose the method as defined above, additionally comprising a step of selecting the joystick unit such that the joystick unit comprises a base and a button jointly connected to the base, such that movement of the button results in movement of the endoscope; further wherein the movement of the button is proportional to the movement of the endoscope.

It is another object of the invention to disclose the method as defined above, additionally comprising a step of selecting the joystick unit such that the joystick unit comprises a touchscreen, such that a touch and a movement on the touchscreen results in movement of the endoscope; further wherein the touch and movement on the touchscreen is proportional to the movement of the endoscope.

It is another object of the invention to disclose the method as defined above, additionally comprising a step of selecting the joystick unit comprising at least one sound sensor, adapted to sense predetermined sound patterns; the joystick unit adapted to operate the maneuvering system based on the predetermined sound patterns.

It is another object of the invention to disclose the method as defined above, additionally comprising a step of providing means adapted to restrain the velocity of the endoscope such that when the means are activated, the velocity of the endoscope is restrained.

It is another object of the invention to disclose the method as defined above, additionally comprising a step of providing the joystick unit with n sensors, where n is an integer larger than one.

It is another object of the invention to disclose the method as defined above, additionally comprising a step of selecting the sensors from a group consisting of a motion sensor, a heat sensor, an electric sensor, a sound sensor, a pressure sensor, an optical sensor and any combination thereof.

It is another object of the invention to disclose the method as defined above, additionally comprising a step of activating at least one of the n sensors in case of power failure.

It is another object of the invention to disclose the method as defined above, additionally comprising a step of activating at least one of the n sensors when the system is connected to power.

It is another object of the invention to disclose the method as defined above, additionally comprising a step of characterizing the joystick unit by an external surface.

It is another object of the invention to disclose the method as defined above, additionally comprising a step of using at least one motion sensor to detect motion upon the external surface.

It is another object of the invention to disclose the method as defined above, additionally comprising a step of using at least one pressure sensor to detect motion perpendicular to the external surface.

It is another object of the invention to disclose the method as defined above, additionally comprising a step of setting the motion of the endoscope to a predetermined value if the speed of the motion as commanded by the joystick unit is above a predetermined value.

It is another object of the invention to disclose the method as defined above, additionally comprising a step of adapting the at least one heat sensor to sense temperatures in the range of about 35 to about 42 degrees.

It is another object of the invention to disclose the method as defined above, additionally comprising a step of enabling maneuvering the endoscope when at least one heat sensor senses temperatures in the range of about 35 to about 42 degrees.

It is another object of the invention to disclose the method as defined above, additionally comprising a step of adapting at least one heat sensor to provide a thermal image, where the at least one heat sensor is coupled to a processing unit adapted to provide the maneuvering system user with the thermal image.

It is another object of the invention to disclose the method as defined above, additionally comprising a step of enabling maneuvering the endoscope upon analysis of the image by the processing system and detection of a human hand; further comprising a step of preventing maneuvering of the endoscope at such times as the analysis of the image by the processing unit fails to detect an image of a human hand.

It is another object of the invention to disclose the method as defined above, additionally comprising a step of adapting at least one electric sensor to sense power failure.

It is another object of the invention to disclose the method as defined above, additionally comprising a step of adapting at least one electric sensor to sense the electric conductivity of the subject's body.

It is another object of the invention to disclose the method as defined above, additionally comprising a step of maneuvering the endoscope upon sensing the conductivity of the subject's body by at least one electric sensor; further comprising a step of preventing maneuvering of the endoscope at such times as the sensor fails to sense the conductivity of the subject's body.

It is another object of the invention to disclose the method as defined above, additionally comprising a step of adapting at least one sound sensor to sense at least one predetermined sound pattern.

It is another object of the invention to disclose the method as defined above, additionally comprising a step of maneuvering the endoscope according to at least one predetermined sound pattern detected by at least one sound sensor.

It is another object of the invention to disclose the method as defined above, additionally comprising a step of adapting at least one pressure sensor to sense pressure applied to the joystick unit.

It is another object of the invention to disclose the method as defined above, additionally comprising a step of altering the activation state of the SFME in a manner selected from a group consisting of: activating the SFME when the pressure sensed by the at least one pressure sensor is above a predetermined value, de-activating the SFME, when the pressure sensed by the at least one pressure sensor is above a predetermined value, and de-activating the SFME when the pressure sensed by the at least one pressure sensor is below a predetermined threshold.

It is another object of the invention to disclose the method as defined above, additionally comprising a step of adapting at least one optical sensor to sense visual changes according to at least one predetermined visual pattern.

It is another object of the invention to disclose the method as defined above, additionally comprising a step of maneuvering the endoscope according to at least one predetermined visual pattern.

It is another object of the invention to disclose the method as defined above, additionally comprising a step of providing an interface system adapted to enable communication between a joystick unit and a maneuvering system unit.

It is another object of the invention to disclose the method as defined above, additionally comprising a step of providing a communication means comprising a member of a group consisting of a wired communication means, a wireless communication means and any combination thereof.

It is another object of the invention to disclose the method as defined above, additionally comprising a step of providing the SFME comprising at least one second joystick unit adapted to zoom the endoscope by means of the maneuvering system unit.

It is another object of the invention to disclose the method as defined above, additionally comprising a step of wearing the second joystick unit by the maneuvering system user.

It is another object of the invention to disclose the method as defined above, additionally comprising a step of coupling the second joystick unit to at least one surgical tool.

It is another object of the invention to disclose the method as defined above, additionally comprising a step of selecting the at least one surgical tool to be an endoscope.

It is another object of the invention to disclose the method as defined above, additionally comprising a step of adapting the at least one joystick unit to control and to direct the endoscope via the maneuvering system on the surgical instrument to which the activated wearable operator is coupled.

It is another object of the invention to disclose the method as defined above, additionally comprising a step of enabling selection of the at least one instrument is obtained by activating the at least one joystick unit; further wherein the activation of the at least one joystick unit is obtained by depression of the joystick unit, voice activating the same, prolonged depression on the same, double clicking on the same and any combination thereof.

It is another object of the invention to disclose the method as defined above, additionally comprising steps of:
a. providing at least one wearable operator comprising at least one wireless transmitter, adapted to transmit a signal once the at least one wearable operator is activated; the at least one wearable operator is either wire or wirelessly in communication with at least one surgical instrument;
b. providing at least one wireless receiver; adapted to receive the signal sent by the transmitter;
c. providing at least one laparoscopy computerized system, in communication with the wireless receiver, adapted to provide a visual onscreen depiction of the at least one instrument to be selected following the activation of the at least one wearable operator; and,
d. providing at least one video screen; wherein the system is adapted to control and to direct the endoscope via the laparoscopy computerized system and the maneuvering system on the instrument to be selected following the activation of the at least one wearable operator.

It is another object of the invention to disclose the method as defined above, additionally comprising steps of providing communication between the at least one of the wearable operators and the instrument via either wire or wirelessly coupling.

It is another object of the invention to disclose the method as defined above, additionally comprising steps of wearing the wearable operator by the surgeon on a predetermined body part.

It is another object of the invention to disclose the method as defined above, additionally comprising steps of selecting the predetermined body part from a group consisting of: the hand of the surgeon, at least one of the fingers of the surgeon, the thigh of the surgeon, the neck of the surgeon, at least one of the legs of the surgeon, the knee of the surgeon, the head of the surgeon and any combination thereof.

It is another object of the invention to disclose the method as defined above, additionally comprising steps of selecting the shape of the wearable operator from a group consisting of a ring, a bracelet and any combination thereof.

It is another object of the invention to disclose the method as defined above, additionally comprising steps of coupling the wearable operator to a predetermined location on the instrument by means of an adaptor.

It is another object of the invention to disclose the method as defined above, additionally comprising steps of providing the wearable operator adjustable so as to fit the predetermined location of the different instruments, each of which is characterized by a different size and shape.

It is another object of the invention to disclose the method as defined above, additionally comprising steps of providing the wearable operator comprising a body having at least two portions at least partially overlapping each other; the two portions are adapted to grasp and hold either the instrument or the predetermined body part there-between, such that a tight-fit coupling between the two portions and the instrument or the predetermined body part is obtained.

It is another object of the invention to disclose the method as defined above, additionally comprising steps of providing one of the two portions rotationally movable relative to the other, such that when the wearable operator is coupled to the instrument, fine-tuned movement of the two body portions is obtainable so as to provide the tight-fit coupling between the two portions and the instrument or the predetermined body part.

It is another object of the invention to disclose the method as defined above, additionally comprising steps of providing the two portions rotationally movable relative to each other, such that when the wearable operator is coupled to the instrument, fine-tuned movement of the two body portions is obtainable so as to provide the tight-fit coupling between the two portions and the instrument or the predetermined body part.

It is another object of the invention to disclose the method as defined above, additionally comprising steps of providing the wearable operator comprising (a) at least one flexible and stretchable strip; and (b) loop-closing means adapted to close a loop with the at least one flexible and stretchable strip; the at least one flexible and stretchable strip and the loop-closing means are provided so as to fit the wearable operator to at least one selected from a group consisting of (a) the predetermined location of the different instruments; (b) the predetermined body part of the surgeon, each of which is characterized by a different size and shape.

It is another object of the invention to disclose the method as defined above, additionally comprising steps of making the flexible and stretchable strip of material selected from a group consisting of silicone, rubber and any combination thereof.

It is another object of the invention to disclose the method as defined above, additionally comprising steps of adapting the wireless transmitter to locate the position of at least one of the instruments.

It is another object of the invention to disclose the method as defined above, additionally comprising steps of selecting the at least one instrument by activating the at least one wearable operator; further wherein the activation of the at least one wearable operator is obtained by depression on a predetermined location in the wearable operator, voice activating the same, prolonged depression on the same, double clicking on the same and any combination thereof.

It is another object of the invention to disclose the method as defined above, additionally comprising steps of the directing the endoscope by the laparoscopy computerized system by using image information shown on the video screen without the help of assistants.

It is another object of the invention to disclose the method as defined above, additionally comprising steps of providing the conventional laparoscopy computerized system comprising at least one surgical instrument spatial location software, adapted to locate the 3D spatial position of the at least one instrument; further wherein the conventional laparoscopy computerized system comprises at least one automated assistant maneuvering system; the automated assistant maneuvering system is coupled to the endoscope and is adapted to direct the endoscope to the at least one instrument, the instrument selected following the activation of the at least one wearable operator.

It is another object of the invention to disclose the method as defined above, additionally comprising steps of matching each transmitted signal from the wearable operator and the wireless transmitter to at least one of the instruments.

It is another object of the invention to disclose the method as defined above, additionally comprising a step of providing a single device comprising the joystick unit and the second joystick unit.

It is another object of the invention to disclose the method as defined above, additionally comprising steps of:
1. providing a maneuvering system comprising:
   a. a first mechanism, comprising:
      i. at least one first coaxial transmission means 101; the first coaxial transmission means 101 defines a first plane; the first coaxial transmission means 101 is characterized by a first axis of rotation; the first axis of rotation is substantially orthogonal to the first plane;
      ii. at least one second coaxial transmission means 102; the second coaxial transmission means 102 defines a second plane and a second axis of rotation; the second axis of rotation is substantially orthogonal to the second plane; the second coaxial transmission means 102 is rotatably connected to the first coaxial transmission means 101; where the first plane is substantially orthogonal to second plane; and
      iii. at least one first means 106 adapted to rotate the first coaxial transmission means 101 around the first axis of rotation;
   b. a second mechanism, comprising:
      i. at least one third coaxial transmission means 103; the third coaxial transmission means 103 defines a third plane; the third coaxial transmission means 103 is characterized by a third axis of rotation; the third axis of rotation is substantially orthogonal to the third plane;

ii. at least one fourth coaxial transmission means 104; the fourth coaxial transmission means 104 defines a fourth plane and a fourth axis of rotation; the fourth axis of rotation is substantially orthogonal to the fourth plane; the fourth coaxial transmission means 104 is rotatably connected to the third coaxial transmission means; where the fourth plane is substantially orthogonal to the third plane;

iii. at least one fifth coaxial transmission means 105; the fifth coaxial transmission means 105 defines a fifth plane and a fifth axis of rotation; the fifth axis of rotation is substantially orthogonal to the fifth plane; the fifth coaxial transmission means 105 is rotatably connected to the fourth coaxial transmission means 104; where the fifth plane is substantially orthogonal to the fourth plane;

iv. at least one second means 107 adapted to rotate the third coaxial transmission means 103 around third axis of rotation;

2. positioning the first coaxial transmission means 101 orthogonally to the second coaxial transmission means 102; the positioning enables transmission of rotation between the first coaxial transmission means 101 and the second coaxial transmission means 102;

3. positioning the third coaxial transmission means 103 orthogonally to the fourth coaxial transmission means 104; the positioning enables transmission of rotation between the third coaxial transmission means 103 and the fourth coaxial transmission means 104;

4. positioning the fourth coaxial transmission means 104 orthogonally to the fifth coaxial transmission means 105; the positioning enables transmission of rotation between the fourth coaxial transmission means 104 and the fifth coaxial transmission means 105;

5. coupling the second coaxial transmission means 102 to the endoscope 200 and the fifth coaxial transmission means 105 to the endoscope 200; the coupling enables rotation of endoscope 200 proportional to rotation of the second coaxial transmission means 102 and the fifth coaxial transmission means 105; and 6. maneuvering the endoscope 200 in at least two degrees of freedom (DOF); maneuvering of the endoscope 200 in at least two degrees of freedom are in the second axis of rotation and in the fifth axis of rotation;

wherein maneuvering in a first DOF of the at least two DOF is performed by rotating the first coaxial transmission means 101 thereby transmitting rotation to the endoscope 200; wherein maneuvering in a second DOF of at least two DOF is performed by rotating the third coaxial transmission means 103 thereby transmitting rotation to the endoscope 200, such that the angle between the second axis of rotation and the fifth axis of rotation is an angle A.

It is another object of the invention to disclose the method as described above, additionally comprising a step of defining angle A to be in the range of about 0 degrees to about 180 degrees.

It is another object of the invention to disclose the method as defined above, additionally comprising a step of providing at least one third mechanism in communication with the first mechanism and the second mechanism, the third mechanism comprising (i) at least one pivoting support adapted to be pivotally attached to the endoscope; the pivoting support adapted to enable the endoscope 200 to pivot around the pivoting support; and (ii) at least one joint 114 mechanically connected to the pivoting support 111, thereby enabling the endoscope 200 to rotate freely in two orthogonal axes around an insertion point; the endoscope pivotally attached to the joint and the pivoting support can pivot at the insertion point independent of the distance between the pivoting support, the joint, and the insertion point; the third mechanism coupled at its distal end to the endoscope 200 and at its proximal end the same is coupled to at least one mechanism selected from a group consisting of the first mechanism, the second mechanism and any combination thereof; and the second joint is located at a predetermined distance from the first joint.

It is another object of the invention to disclose the method as defined above additionally comprising a step of providing the pivoting support comprising a gimbal.

It is another object of the invention to disclose the method as defined above, additionally comprising a step of providing the joint 114 comprising a gimbal.

It is another object of the invention to disclose the method as defined above, additionally comprising a step of providing at least one zoom mechanism adapted to maneuver the endoscope along the main longitudinal axis of the same.

It is another object of the invention to disclose the method as defined above, additionally comprising a step of providing the zoom mechanism 200 comprising clasping means adapted to enable reversible reciprocating movement along the main longitudinal axis of the same.

It is another object of the invention to disclose the method as defined above, additionally comprising a step of operating the zoom mechanism by at least one motor.

It is another object of the invention to disclose the method as defined above, additionally comprising a step of providing the third mechanism with a plurality of q joints, at least one of which is coupled to the pivoting support, and at least one of which is coupled to the second mechanism; where q is an integer greater than or equal to one.

It is another object of the invention to disclose the method as defined above, additionally comprising a step of selecting the first coaxial transmission means 101, the second coaxial transmission means 102, the third coaxial transmission means 103, the fourth coaxial transmission means 104, and the fifth coaxial transmission means 105 from a group consisting of gearwheels, wheels, crown gears, bevel gears, spur gears, belts, and any combinations thereof.

It is another object of the invention to disclose the method as defined above, additionally comprising a step of providing the system with attaching means adapted to reversibly couple the maneuvering system unit to a hospital bed.

It is another object of the invention to disclose the system as defined above, additionally comprising a step of selecting the attaching means from a group consisting of mechanical means, magnetic means and any combination thereof.

It is another object of the invention to disclose the method as defined above, additionally comprising a step of selecting the mechanical attaching means from a group consisting of clip, a fastening element, non-adhesive tape, adhesive tape, a snap fastener, a button and any combination thereof.

It is another object of the invention to disclose the method as defined above, additionally comprising a step of providing magnetic attaching means with at least one magnet, the at least one magnet selected from a group consisting of a ferromagnet, a paramagnet, and any combination thereof; where the magnetic means is attached to one selected from a group consisting of a hospital bed, a maneuvering system unit, and any combination thereof.

It is another object of the invention to disclose the method as defined above, additionally comprising a step of defining an angle $\theta$ for the rotation in the second plane of the maneuvering system unit.

It is another object of the invention to disclose the method as defined above, additionally comprising a step of defining angle θ of the SFME to vary between 0 and about 360 degrees, preferably between 0 and about 160 degrees.

It is another object of the invention to disclose the method as defined above, additionally comprising a step of defining an angle ψ for the rotation in the second plane of the maneuvering system unit.

It is another object of the invention to disclose the method as defined above, additionally comprising a step of defining angle ψ of the SFME to vary between 0 and about 360 degrees, preferably between 0 and about 140 degrees.

It is another object of the invention to disclose the method as defined above, additionally comprising a step of providing the SFME to control rotation of the maneuvering system unit in angle ψ and angle θ.

It is another object of the invention to disclose the method as defined above, additionally comprising a step of enabling control of movement of the joystick unit in any direction selected from a group consisting of ψ, θ, and any combination thereof, such that movement of the endoscope is in same direction as the movement of the joystick unit and the movement is proportional to one selected from a group consisting of the movement of the joystick unit, the speed of movement of the joystick unit and any combination thereof.

It is another object of the invention to disclose the method, additionally comprising a step of providing the system with a quick release handle adapted to disassemble the endoscope from the maneuvering system unit.

It is another object of the invention to disclose the method as defined above, additionally comprising a step of providing the first mechanism with locking means adapted to maintain in a predetermined orientation upon power failure; and to prevent any rotational movement of at least one selected from a group consisting of the first coaxial transmission means 101, the second coaxial transmission means 102 and any combination thereof.

It is another object of the invention to disclose the method as defined above, additionally comprising a step of providing the second mechanism with locking means adapted to maintain in a predetermined orientation upon power failure; and to prevent any rotational movement of at least one selected from a group consisting of the first coaxial transmission means 101, the second coaxial transmission means 102 and any combination thereof.

BRIEF DESCRIPTION OF THE FIGURES

In order to understand the invention and to see how it may be implemented in practice, a few preferred embodiments will now be described, by way of non-limiting example only, with reference to be accompanying drawings, in which

FIGS. 2a-d present wearable operators and a free-standing operator;

FIG. 11-14 shows different configurations for the motors of a maneuvering system unit for maneuvering an endoscope;

DETAILED DESCRIPTION OF THE INVENTION

Figure 1A:
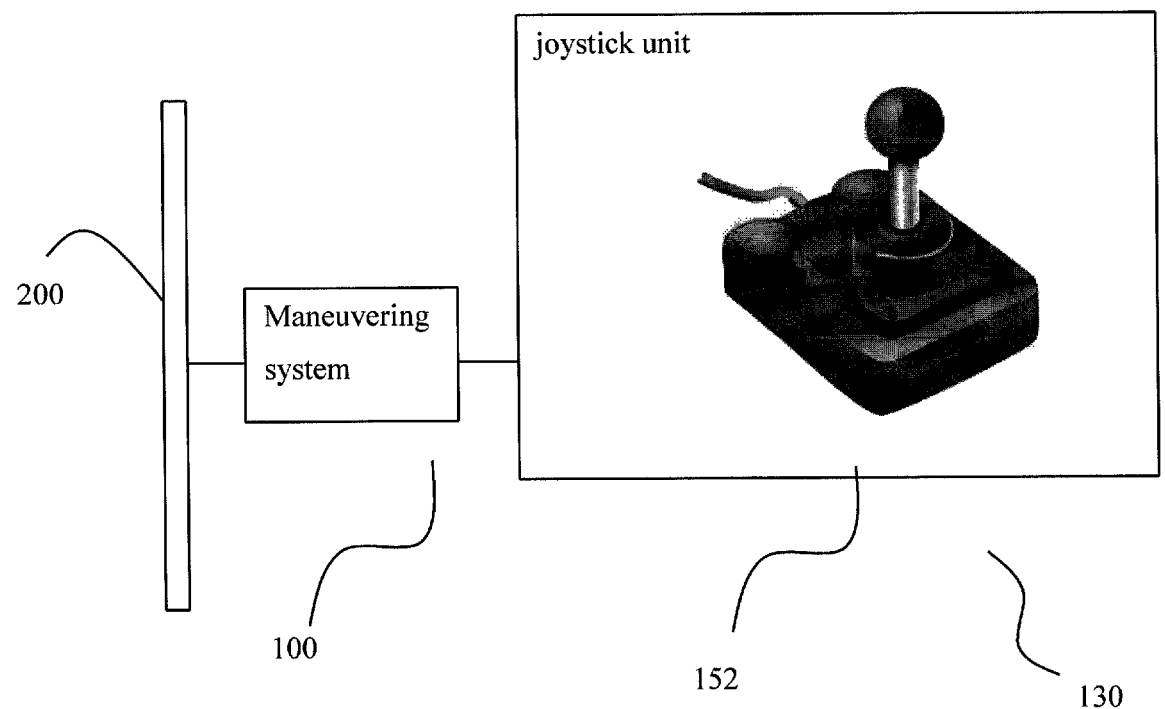
FIGS. 1a and 1b present a system for controlling an endoscope in different configurations.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The present invention discloses a system for maneuvering an endoscope (SFME) for maneuvering an endoscope, comprising (a) at least one maneuvering system unit, adapted to maneuver an endoscope in at least two degrees of freedom (DOF); and (b) at least one joystick unit in communication with the maneuvering system unit, adapted to operate the maneuvering system unit; wherein at least one of the movement of the joystick unit and movement on the joystick unit results in movement of the endoscope by means of the maneuvering system unit.

The present invention additionally provides a method for maneuvering an endoscope comprising steps of:
a. providing at least one endoscope;
b. providing a system for maneuvering an endoscope (SFME), the SFME comprising:
  i. at least one maneuvering system; and
  ii. at least one joystick unit in communication with the maneuvering system, adapted to operate the maneuvering system;
c. coupling the endoscope to the SFME; and
d. maneuvering the joystick unit,
thereby maneuvering the endoscope and controlling the movements of the same.

The term 'non-human animal' refers hereinafter to any living animal, including, but not limited to, mammals, birds, reptiles, amphibians and fish.

The term 'region of interest' refers hereinafter to any region within the body of a subject which may be of interest for the operator of the system of the present invention. The region of interest may be, for example, an organ to be operated on, a restricted area which a surgical instrument should avoid approaching, or any other region within the human body or body of another living animal.

The term 'surgical environment' refers hereinafter to any anatomical part within the body of a subject which may be in the surroundings of a surgical instrument. The environment may comprise: organs, body parts, walls of organs, arteries, veins, nerves, a region of interest, or any other anatomical part of the human body.

The terms 'surgical instrument' and 'surgical tool' refer hereinafter to any device used by medical personnel, including, but not limited to, a scalpel, a retractor, a clamp, a swab, a needle, an endoscope, and any other medical tool or instrument.

The term 'endoscope' refers hereinafter to any means adapted for looking inside the body for medical reasons. This may be any instrument used to examine the interior of a hollow organ or cavity of the body. The endoscope may also refer to any kind of a laparoscope.

The term 'spatial position' refers hereinafter to a predetermined spatial location and/or orientation of an object (e.g., the spatial location of the endoscope, the angular orientation of the endoscope, and any combination thereof).

The term 'degrees of freedom' (DOF) refers hereinafter to a set of independent displacements that specify completely the displaced position of the endoscope or laparoscope as defined above.

The term 'insertion point' refers hereinafter to the point where the endoscope enters the human body.

The term 'joystick unit' refers hereinafter to a motion and position sensitive device enabled to control the motion of another device, with the motion and position information including, but not limited to, the direction of motion (in 1, 2 or 3 dimensions) and the speed of the motion and the changes in direction and speed as a function of time. Joystick units may, for example, in a non-limiting manner, be shaped like a rod or lever; which is bent, twisted, depressed or slid, the direction of the bend, twist, depression or sliding relatable to the direction of motion and the magnitude thereof relatable to the speed of the motion. Joystick units can comprise a button which is depressed, slid or rocked, wherein the direction of the depression, sliding or rocking is related to the direction of motion and the magnitude thereof is related to the speed of the motion. They can comprise a surface along which a finger or fingers or a hand or an implement slides, wherein the direction of the motion on the surface is related to the direction of motion and the speed of the motion along the surface is related to the speed of motion of the controlled device.

The term "about" refers hereinafter to a range of +−25% of the discussed quantity.

All temperatures referred to herein are temperatures in degrees Celsius.

The following abbreviations are used throughout the disclosure:
  DOF refers to degree(s) of freedom;
  SFME refers to System For Maneuvering an Endoscope, a system for enabling an operator to maneuver the endoscope as disclosed hereinbelow;
  FCTM refers to first coaxial transmission means;
  SCTM refers to second coaxial transmission means;
  TCTM refers to third coaxial transmission means;
  FOCTM refers to fourth coaxial transmission means; and,
  FTCTM refers to fifth coaxial transmission means.

Figure 1B:
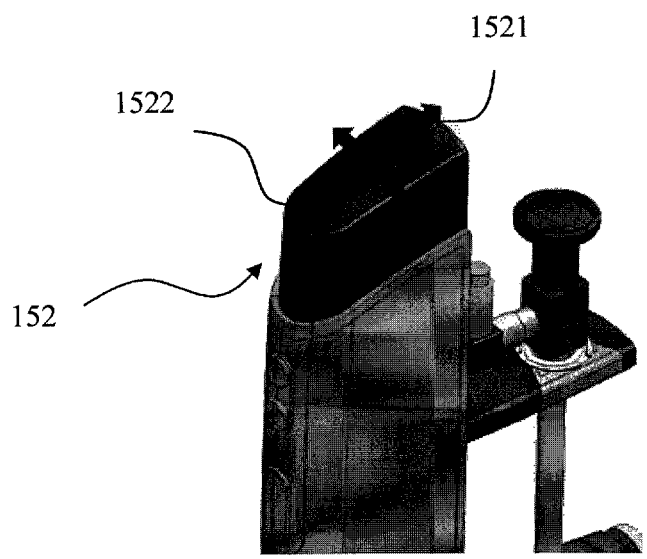

Reference is now made to FIGS. 1a and 1b, which present in a non-limiting manner the system for maneuvering an endoscope (SFME) 130 according to the present invention.

The system for maneuvering an endoscope 130 comprises at least one joystick unit 152 and at least one communication means. At least one of the at least one communication means is adapted to connect at least one joystick unit 152 to any standard maneuvering system 100 for maneuvering an endoscope 200. Different joystick units can control different aspects of the endoscope's motion, for non-limiting example, a joystick unit to control lateral movement of the endoscope, a joystick unit to control zooming and a joystick unit to control articulation of the endoscope tip.

The communication means can comprise a wireless communication means, a wired communication means and any combination thereof.

The connection between the joystick unit 152 and the maneuvering system 100 (or other control system) enables control of the maneuvering system 100 by the joystick unit 152, thereby enabling an operator to control the movement of the endoscope 200 by controlling the joystick unit 152.

Furthermore, the communication means is adapted to disconnect the joystick unit 152 from the maneuvering system 100, thereby preventing the endoscope 200 from being moved by the joystick unit 152. Disconnection of the joystick unit 152 prevents the situation of unwanted movement of the endoscope 200 due to inadvertent joystick unit 152 motion. Thus, in such a situation, movement of the joystick unit 152 will not result in movement of the endoscope 120.

FIG. 1b illustrates a closer view of the joystick unit 152. Upon pressing the joystick unit 152 in the direction of arrow 1521, the endoscope moves forward or backward. Upon pressing the joystick unit 152 in the direction of arrow 1522, the endoscope moves left or right.

In the best embodiments, movement of the endoscope is proportional to movement of the joystick unit, unless the speed of the endoscope tip in a given direction would be above a predetermined value. In these embodiments, movement of the endoscope at speeds greater than the predetermined value is prevented. In preferred embodiments, if a speed above the predetermined value is commanded, the endoscope will continue moving, but with a speed at or just below the predetermined value. In some embodiments, if a speed above the predetermined value is commanded, movement of the endoscope is prevented.

According to another embodiment of the present invention, the SFME 130 may be wearable, either by a user or by an instrument. Reference is now made to FIGS. 2a-2d which depict, in a non-limiting manner, a wearable operator. FIGS. 2a and 2b depict the at least one joystick unit 152 mounted in a operator 150, here a ring wearable by a user, while FIG. 2c depicts the at least one joystick unit 152 mounted on a operator 150 attached to an exemplary surgical instrument and FIG. 2d depicts a operator 150 to be held in the hand. The operator 150 can be attached to any surgical instrument, can be attached to or mounted on the endoscope, or, as shown in FIG. 2d, can be a free-standing unit which can sit on, for example, the operating table, a side table or stand, or on a hospital bed.

Referring again to FIGS. 2a-d, FIGS. 2a and 2c depict embodiments of operator 150 with a single joystick unit 152, while FIGS. 2b and 2d depict embodiments of the operator with two joystick units 152. In preferred embodiments of devices such as FIGS. 2a and 2c with a single joystick unit, the joystick unit 152 controls maneuvering of the endoscope. In less-preferred embodiments, the joystick unit controls zoom of the endoscope. In embodiments of the operator 150 such as FIGS. 2b and 2d with two joystick units, one joystick unit 152 controls maneuvering of the endoscope, while the other joystick unit 152 controls zoom of the endoscope.

Referring again to FIGS. 2a-2b, according to some embodiments, the wearable operator 150 is adjustable by means of flexible and stretchable silicone and/or rubber strip 154 and a loop-closing means 156. The loop-closing means 156 is adapted to close a loop with the flexible and stretchable strip. Together, the flexible and stretchable strip and the loop-closing means are provided so as to fit the wearable operator to at least one selected from a group consisting of (a) said predetermined location of said different instruments; (b) said predetermined body part of said surgeon, each of which is characterized by a different size and shape.

As will be disclosed hereinafter, the loop-closing means 156 can be e.g., a unidirectional catch, a rack, a peg or any other mechanism known in the art.

According to another embodiment, the silicone and/or rubber strip 154 is passed through a unidirectional catch (e.g., ratchet 156), such that, when the physician wears the wearable operator 150, he adjusts the same by pulling the silicone and/or rubber strip 154 through the ratchet 156.

According to another embodiment, the silicone and/or rubber strip 154 is rotated around rack or peg 156 such that, when the physician wears the wearable operator 150, he adjusts the same by pulling the silicone and/or rubber strip 154 around the peg 156.

According to this embodiment, the silicone and/or rubber strip 154 is characterized by a varied width along its length. More specifically, at least a portion of the silicone and/or rubber strip 154 is characterized by a greater width, such that when the same is twisted/rotated around peg 156 and reaches the wider portion, the same is fixedly secured to the wearable operator 150.

According to another embodiment, the silicone and/or rubber strip 154 is characterized by different surface roughnesses along its length. More specifically, at least a portion of the silicone and/or rubber strip 154 is characterized by e.g., an abrasive or rough surface such that when the same is twisted/rotated around peg 156 and reaches the rougher portion, the same is fixedly secured to the wearable operator 150.

Referring again to FIG. 2c illustrating an embodiment of the wearable operator 150 attached to a surgical tool via fastener 155. Some embodiments of fastener 155 are shown in FIGS. 2e-2i.

Figure 2E:
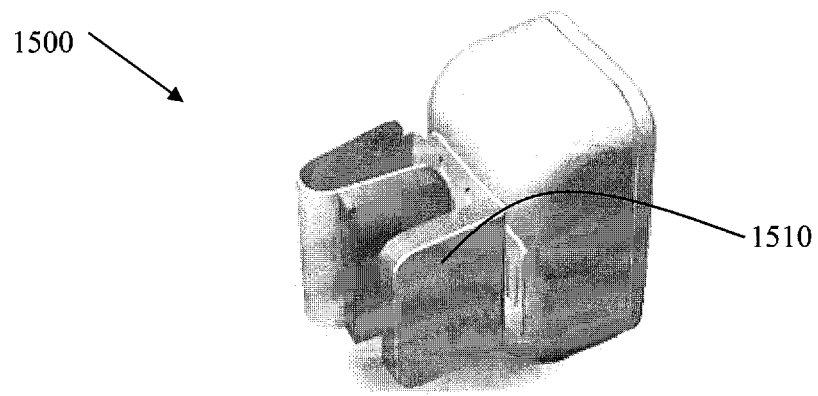
FIGS. 2e-i present the fastener for a wearable operator.

According to the embodiment shown in FIG. 2e, the wearable operator 150 comprises a unidirectional coupling (e.g., ratchet 1510).

Once the wearable operator 150 is secured to the surgical tool, the wearable operator 150 is adjusted to the size and dimensions of the surgical tool by means of a unidirectional catch (e.g., ratchet 1510).

Figure 2F:
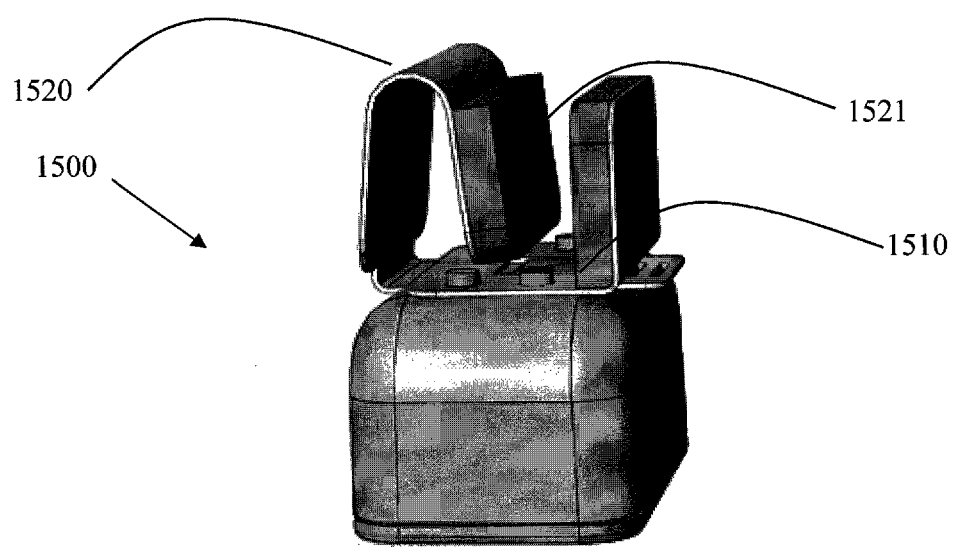
Figure 2G:
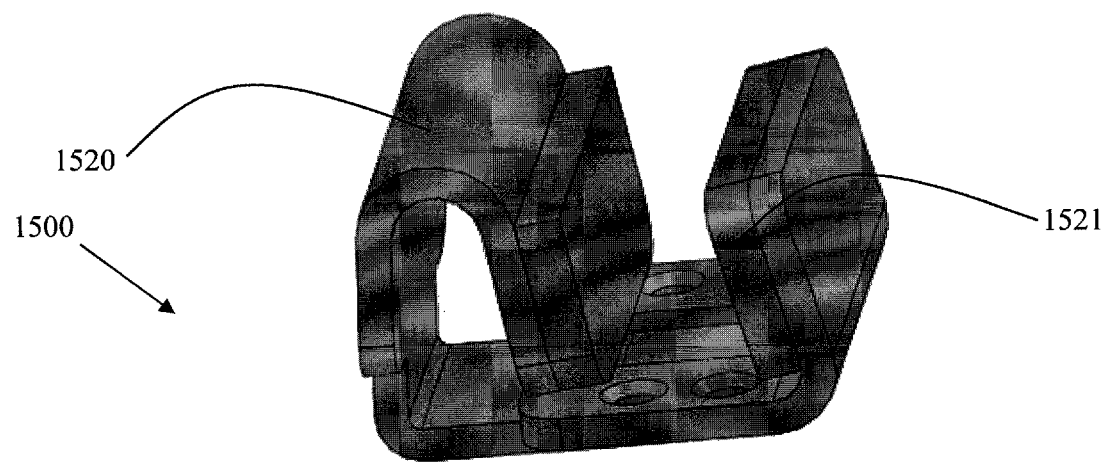

According to another embodiment, the wearable operator 150 comprises a body having at least two portions 1520 and 1521 (see FIG. 2f). Said portions are adapted to 'grasp' the surgical tool such that when the wearable operator 150 is coupled to the surgical tool, fine-tuned movement of the two body portions is obtainable so as to provide said tight-fit coupling between said two portions and said instrument.

According to another embodiment (FIG. 2g), one of the two portions (either 1520 or 1521) is rotationally movable relative to the other, such that when said wearable operator is coupled to said instrument, fine-tuned movement of said two body portions is obtainable so as to provide said tight-fit coupling between said two portions and said instrument.

According to another embodiment (FIG. 2h), the two portions (1521 and 1520) are rotationally movable relative to each other, such that when the wearable operator is coupled to said instrument, fine-tuned movement of said two body portions is obtainable so as to provide said tight-fit coupling between said two portions and said instrument.

Figure 2H:
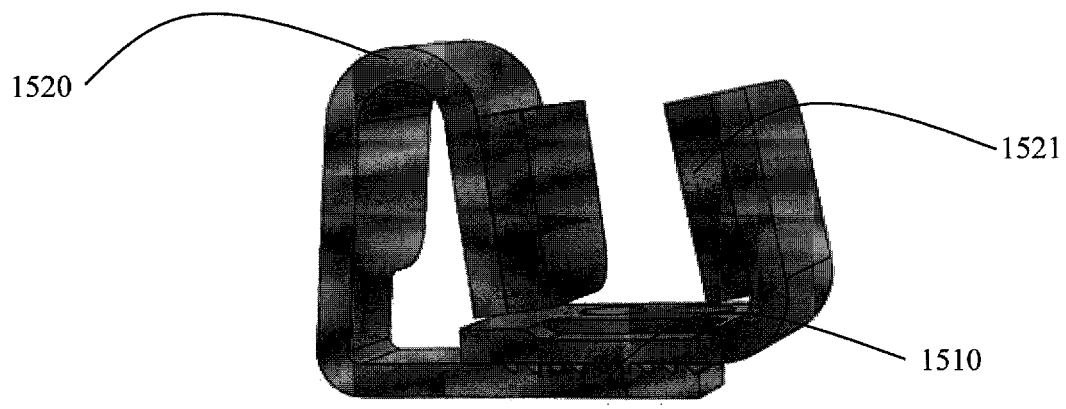

In reference to FIG. 2h, the movement of either portion 1520 or portion 1521 relative to the other is obtained by fixating the position of either portion 1520 or portion 1521 and coupling the other portion to e.g., a unidirectional catch (e.g., ratchet) 1510 or a two-way directional catch 1510 on the body of the wearable operator.

Figure 2I:
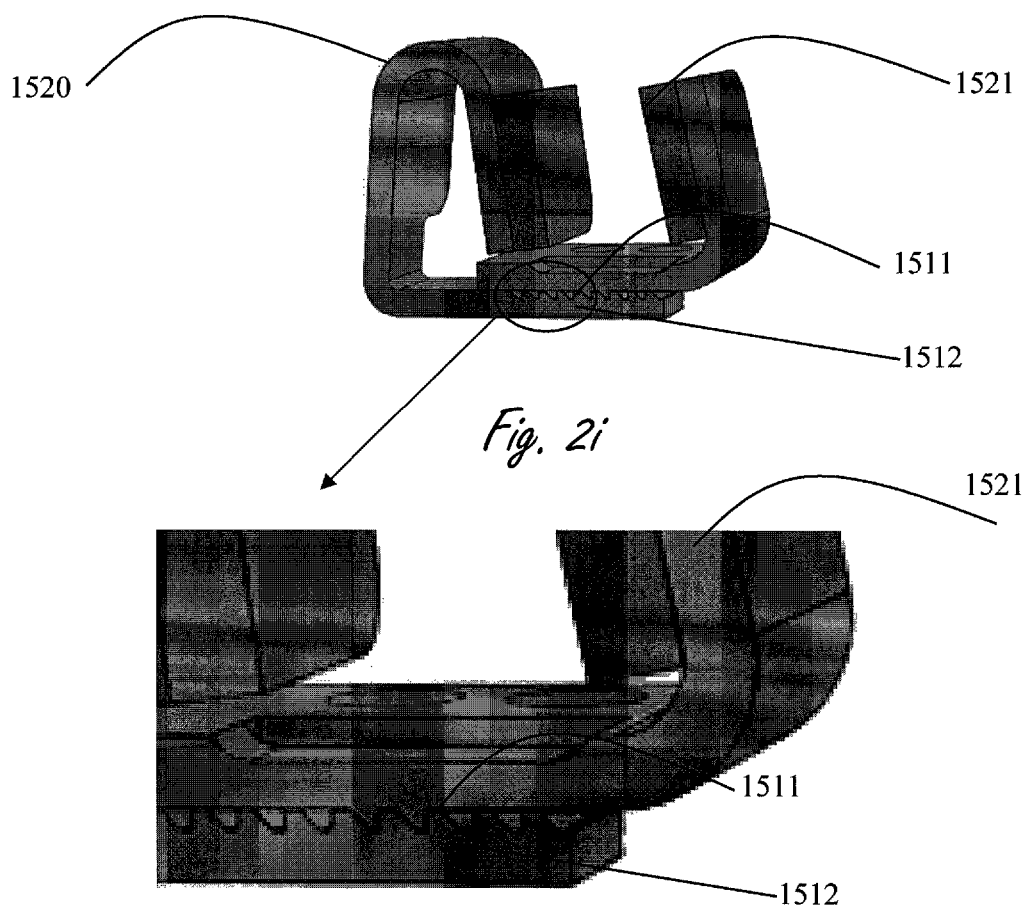

According to another embodiment, the movement of either portion 1520 or portion 1521 relative to the other is obtained by providing one portion, e.g., portion 1521 with cog-like teeth 1511 and the body of the wearable operator with cog-like teeth 1512 matching with cog-like teeth 1511 (see FIG. 2i). In such a way portion 1521 can be linearly moved relative to portion 1520.

Referring again to FIG. 2d, this embodiment of operator 150 depicts joystick unit 152a, which controls maneuvering of the endoscope, comprising a force joystick, while joystick unit 152b, which controls zooming, comprises a pressable button. Button 156 is an emergency off button; pressing button 156 quickly stops all motion. Light 158 is a fault light, illuminating when a fault is detected in the system.

In some embodiments, a single control is used for both lateral maneuvering of the endoscope and zooming of the endoscope. In some variants of these embodiments, lateral movement of the joystick unit or lateral movement of a hand on the joystick unit is translated into lateral maneuvering of the endoscope, for non-limiting example, as described above for FIG. 1b, while pressure on the joystick unit, either continuous pressure or clicking the joystick unit, is translated into zooming of the endoscope, as described hereinbelow.

In other embodiments, two joystick units are used, one for lateral maneuvering of the endoscope, and one for zooming.

In yet other embodiments, two joystick units are used, one for maneuvering, both lateral maneuvering and zoom, and the other for directing the endoscope to focus on a desired tool. In these embodiments, on the display screen showing the field of view of the endoscope, a symbol indicates the tool on which the endoscope is focused. This symbol can be a shape or it can be highlighting. When a user clicks on the second joystick unit, the new tool to be focused on is indicated, either by moving the symbol or highlighting to the new tool, or by a second symbol or a second color of highlighting. The user can repeat clicking until the desired tool is indicated. In some embodiments, ceasing to click on the second joystick unit indicates that the current tool is the desired tool; in other embodiments, a longer pressure on the second joystick unit indicates that the current tool is the desired tool. Once the desired too has been selected, the endoscope redirects to the desired tool.

Operation of the zoom mechanism can be by clicking on a joystick unit or by a continuous pressure on a joystick unit. Some non-limiting examples of embodiments of methods of zoom control include:

1. A single click to select zoom in, a double click to select zoom out, and continuous pressure to zoom at a predetermined rate in the selected direction.
2. A double click to select zoom in, a single click to select zoom out, and continuous pressure to zoom in the selected direction.
3. A single click to change the direction of zoom and continuous pressure to zoom at a predetermined rate in the selected direction.
4. A single click to change the direction of the zoom, a double click to zoom by a predetermined amount in the selected direction.

5. A double click to change the direction of the zoom, a single click to zoom by a predetermined amount in the selected direction.
6. A single click to change the direction of zoom and a double click to zoom by a predetermined amount in the selected direction.
7. A single click to change the direction of zoom, a double click to zoom by a predetermined amount in the selected direction, and continuous pressure to zoom at a predetermined rate in the selected direction.

In embodiments in which continuous pressure is used to zoom in the selected direction, in some variants of these embodiments, continuous pressure above a predetermined minimum pressure (a minimum which can be zero) zooms the endoscope at a predetermined zoom rate. In other variants of embodiments in which continuous pressure is used to zoom in the selected direction, if the pressure is above a predetermined minimum pressure, which can be zero, the greater the pressure, the greater the zoom rate, until a predetermined maximum rate is reached, above which the zoom rate is the predetermined maximum rate.

In embodiments wearable by the user, the operator 150 can be worn as a ring on a finger; as a wristband on the wrist; an armband on an arm; on the chest, either supported around the chest or supported around the neck; or on the head, supported by a headband, by a helmet or by a helmet frame.

The communication means connecting the maneuvering system to the operator 150 can be a wireless communication means, a wired communication means, and any combination thereof.

In other embodiments of the current invention, SFME 130 additionally comprises, in a non-limiting manner, means for controlling movement of endoscope 200 adapted to restrain the endoscope's velocity.

In other embodiments of the current invention, SFME 130 additionally comprises, in a non-limiting manner, n sensors, where n is an integer greater than or equal to one. The sensors may be adapted to activate in case of power failure or to activate when connected to power. The sensors are selected in a non-limiting manner from a group consisting, for example, of motion sensors, heat sensors, electric sensors, sound sensors, pressure sensors, optical sensors, and any combination thereof.

In other embodiments of the current invention, joystick unit 152 is characterized in a non-limiting manner by an external surface.

In other embodiments of the current invention, at least one motion sensor detects motion of joystick unit 152. Furthermore, detection of motion is used for deactivation of the motion of endoscope 200 if the requested speed of the motion is above a predetermined threshold.

In other embodiments of the current invention, at least one motion sensor detects, in a non-limiting manner, motion on the external surface of joystick unit 152. Furthermore, endoscope 200 then moves in response to the motion on the external surface of joystick unit 152. Additionally, detection of motion above a predetermined threshold speed on joystick unit 152 will deactivate motion of endoscope 200.

In other embodiments of the current invention, at least one heat sensor is adapted in a non-limiting manner to sense temperatures in the range of about 35 to about 42 degrees. The at least one heat sensor is adapted to sense whether a human hand/fingers are activating (i.e., touching) the joystick unit 152.

Furthermore, at least one heat sensor enables in a non-limiting manner the activation of SFME 130 when the at least one heat sensor senses temperatures in the range of about 35 to about 42 degrees.

Additionally, at least one heat sensor is adapted in a non-limiting manner to provide a thermal image, where the at least one heat sensor is coupled to a processing unit adapted to provide the endoscope user with the thermal image, and a processing unit enables the activation of SFME 130 upon analysis of the image and detection of human hand.

In other embodiments of the current invention, at least one electric sensor is adapted in a non-limiting manner to detect, for example, a power failure, the electric conductivity of the subject's body, and any combination thereof. Additionally, the conductivity of the subject's body sensed by the at least one electric sensor enables the activation of the SFME.

In other embodiments of the current invention, at least one sound sensor is adapted in a non-limiting manner to sense predetermined sound patterns. Furthermore, the predetermined sound patterns sensed by the at least one sound sensor enables the activation of SFME 130. Additionally, at least one sound sensor is used to operate endoscope 200 according to predetermined sound patterns (e.g., the human voice, predetermined movement commands).

In other embodiments of the current invention, at least one pressure sensor is adapted in a non-limiting manner to sense pressure applied to SFME 130.

Additionally, in some embodiments, the pressure sensed by the at least one pressure sensor is used to activate SFME 130. In some embodiments, when the pressure sensed by the at least one pressure sensor is above a predetermined threshold, SFME 130 is activated. In other embodiments, when the pressure sensed by the at least one pressure sensor is below a predetermined threshold, SFME 130 is de-activated. In other embodiments, when the pressure sensed by the at least one pressure sensor is below a predetermined threshold, SFME 130 is activated.

An example of pressure above a pre-determined threshold activating SFME 130 is a pressure sensor in the joystick unit, which is activated when the pressure of a hand or fingers or an appropriated implement is sensed. SFME 130 would be deactivated if the above pressure was below a pre-determined threshold.

An example of pressure above a pre-determined threshold de-activating SFME 130 is a joystick unit where pressure is used to set the speed of motion of a scalpel. If the pressure is above the pre-determined threshold, the scalpel would move too rapidly, so SFME 130 is de-activated if pressures above the pre-determined threshold are sensed. SFME 130 would then be activated if pressures are below a pre-determined threshold.

In other embodiments of the current invention, at least one optical sensor is adapted in a non-limiting manner to sense visual changes according to predetermined visual patterns. Furthermore, the at least one optical sensor enables the activation of SFME 130 according to predetermined visual patterns. Additionally, at least one optical sensor is used to operate endoscope 200 according to predetermined visual patterns.

In some embodiments, SFME 130 is adapted to sense power failure by any means known in the art, including the sensors described herein. In some embodiments, SFME 130 responds to power failure by instructing the maneuvering system to keep the endoscope and any other controlled instruments in the position and at the angle held by them immediately before the power failure. In some embodiments, the system further comprises means by which the endoscope can be manually switched to manual control in the event of power failure, so that the operation can continue safely with an operating assistant maneuvering the endoscope during the period of power failure.

In some embodiments, the system comprises battery backup such that, in the event of power failure, the system switches automatically to battery power, enabling the SFME to continue to control movement of the endoscope during power outages.

Figure 3:
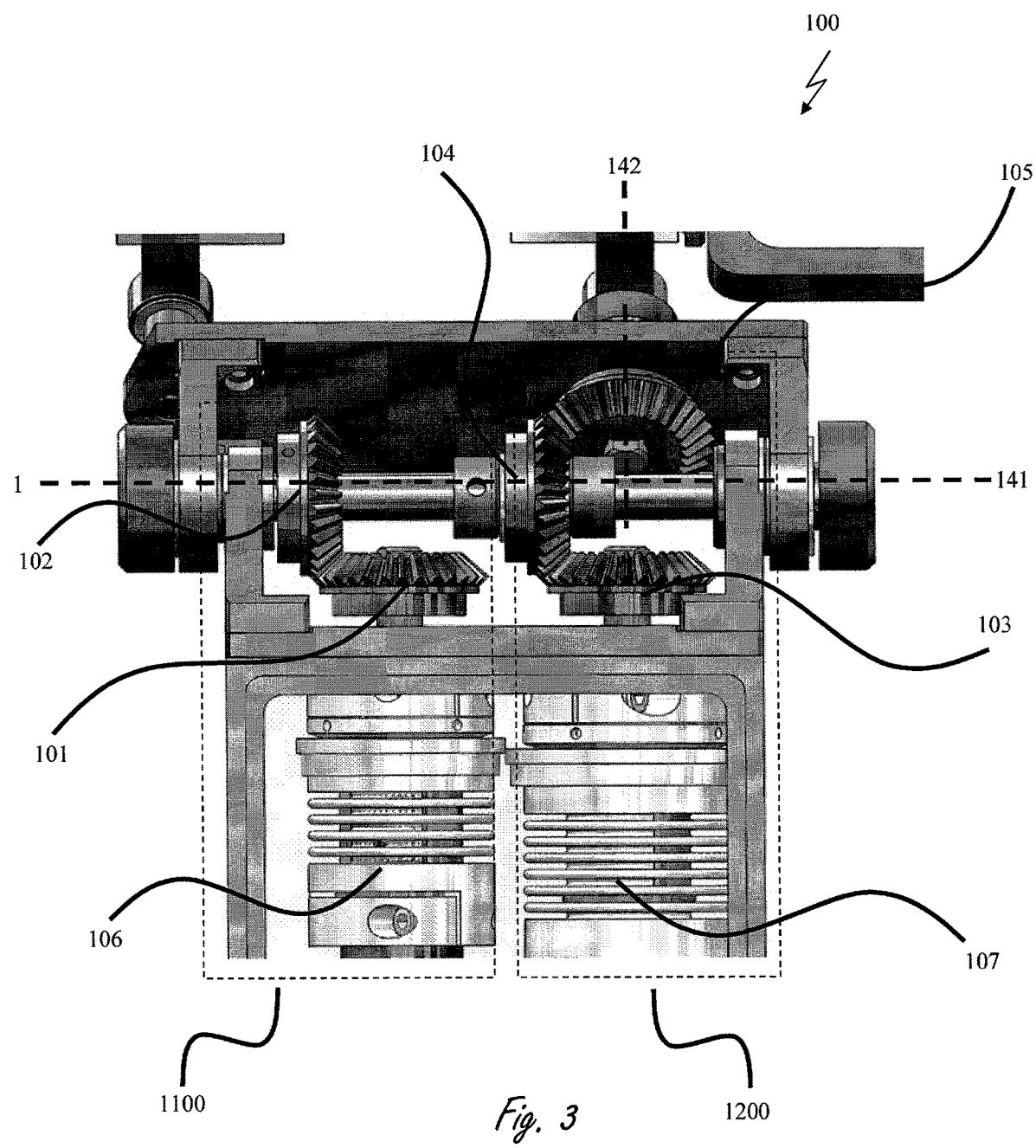
FIG. 3 presents a maneuvering system unit for maneuvering an endoscope.

Reference is now made to FIG. 3, which shows, in a non-limiting manner, a maneuvering system 100 for maneuvering an endoscope 200 (endoscope not shown; at top). The system comprises a first mechanism 1100 for maneuvering an endoscope in one DOF. The first mechanism 1100 comprises (i) at least one first coaxial transmission means (FCTM) 101, FCTM is characterized by a first axis of rotation and a first plane substantially orthogonal to the first axis of rotation; (ii) at least one second coaxial transmission means (SCTM) 102, SCTM is characterized by a second axis of rotation 141 and a second plane substantially orthogonal to the second axis of rotation 141, additionally, the SCTM is rotatably connected to the FCTM; and (iii) at least one first means 106 adapted to rotate FCTM 101 around a first axis of rotation. The FCTM 101 transmits the rotation to the SCTM 102. Additionally, the system also comprises a second mechanism 1200 for maneuvering an endoscope 200 in a second DOF. The second mechanism 1200 comprises (i) at least one third coaxial transmission means (TCTM) 103, TCTM 103 is characterized by a third axis of rotation and a third plane substantially orthogonal to the third axis of rotation; (ii) at least one fourth coaxial transmission means (FOCTM) 104, the FOCTM is characterized by a fourth plane, a fourth axis of rotation substantially orthogonal to fourth plane and rotatably connected to the TCTM 103, where the connection is such that the fourth plane is substantially orthogonal to the third plane; (iii) at least one fifth coaxial transmission means (FTCTM) 105. The FTCTM 105 defines a fifth plane, a fifth axis of rotation 142 substantially orthogonal to fifth plane and rotatably connected to FOCTM 104. The connection is such that the fifth plane is substantially orthogonal to the fourth plane; and (iv) at least one second means 107 adapted to rotate TCTM 103 around the third axis of rotation. The TCTM 103 transmits rotation to FOCTM 104, the FOCTM 104 then transmits rotation to the FTCTM 105. The system than maneuvers the endoscope 200 by adapting the first mechanism to rotate the endoscope 200 in one DOF substantially orthogonal to the second plane (i.e. second axis of rotation 141), and adapting the second mechanism to rotate the endoscope 200 in a second DOF substantially orthogonal to the fifth plane (i.e. fifth axis of rotation 142). The two DOF define two axes of rotation with angle A between them. The angle A is in the range of 0° to 180°.

Figure 4A:
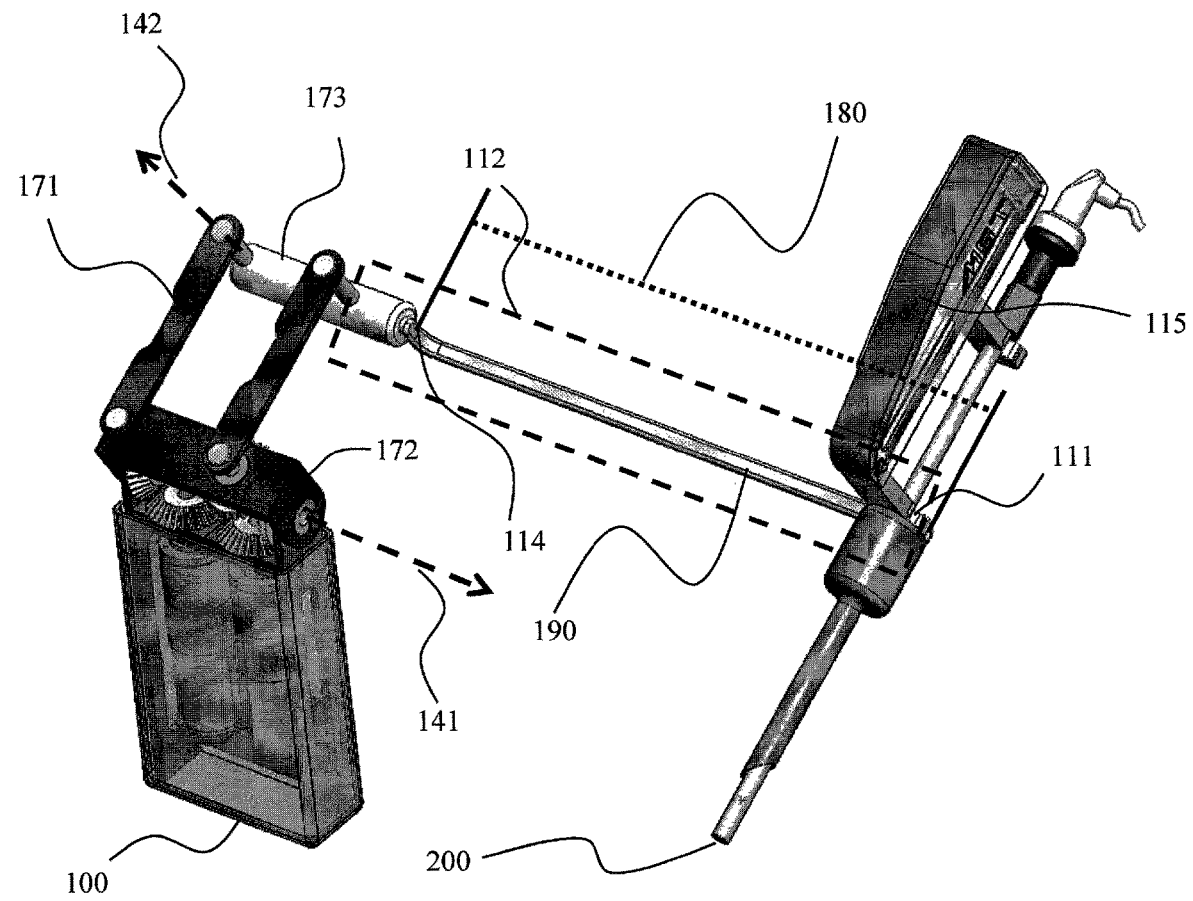
FIGS. 4a and 4b show two configurations of a maneuvering system unit for maneuvering an endoscope additionally attached to a rotating means and the endoscope.
Figure 4B:
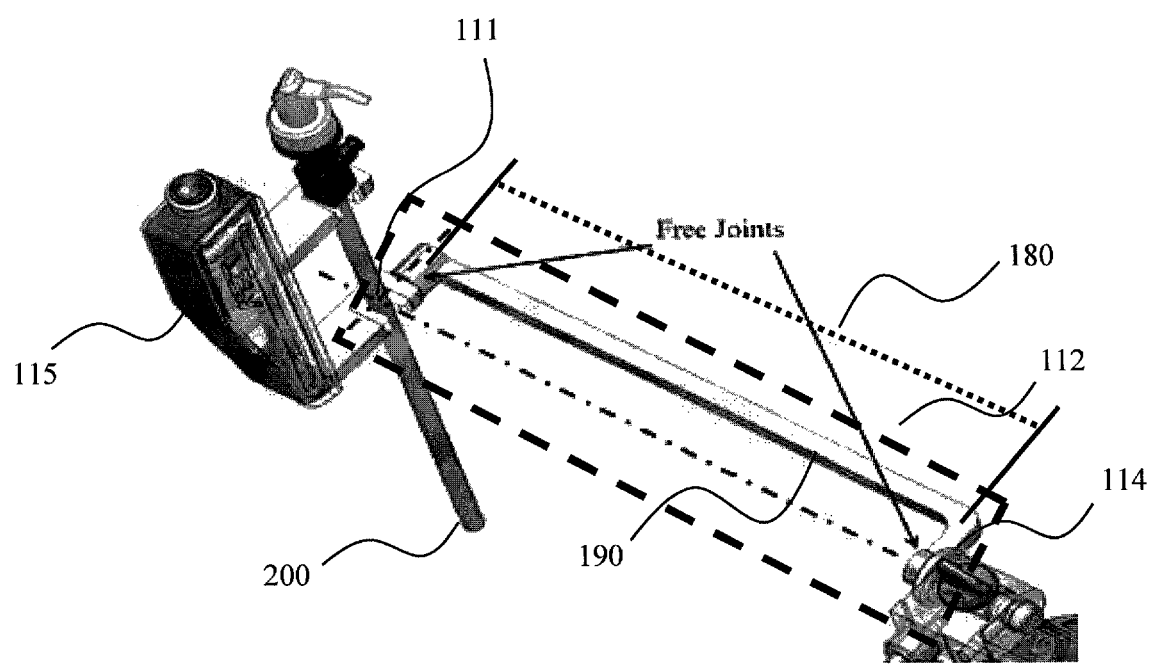

Reference is now made to FIGS. 4a and 4b, which present, in a non-limiting manner, a rotating means in communication with first mechanism 1100 and second mechanism 1200. FIG. 4a illustrates the rotating means from the side, while FIG. 4b illustrates it from above. The rotating means comprises at least one third mechanism 112 for rotating the endoscope 200 independently around two orthogonal axes, the third mechanism 112 comprising at least one pivoting support 111 adapted to be pivotally attached to endoscope 200, pivoting support 111 adapted to enable endoscope 200 to pivot around pivoting support 111; and at least one joint 114 mechanically connected to pivoting support 111 and coupled to a mechanism selected from a group consisting of the first mechanism, the second mechanism and any combination thereof, thereby enabling endoscope 200 to rotate around at least two orthogonal axes and to rotate in the at least two orthogonal axes about the insertion point in the body of a subject.

Joint 114 is coupled to pivoting support 111 by means of a rod, an arm, or n joints (n being an integer greater than or equal to 0).

Joint 114 is located at a predetermined distance 180 from pivoting support 111.

Each of the joints is adapted to provide rotation to pivoting support 111 in at least one of the orthogonal axes, thereby providing flexibility of rotation to endoscope 200.

In the best embodiment, gimbals, pivoting supports or other joint mechanisms at joint 114 and pivoting support 111 enable endoscope 200 to remain fixed at the insertion point and to pivot about its insertion point in the body of the patient without applying force on the patient at the insertion point, especially if the line of application of force to move the endoscope is not completely collinear with the axis of the endoscope.

It should be emphasized that the addition of joint mechanism 114 ensures that no force is applied on the penetration point when the system's center of movement is misaligned with the penetration point.

It should be emphasized that according to a preferred embodiment of the present invention, joint mechanisms 114 and pivoting support 111 are gimbals.

In one embodiment, each of joint mechanisms 114 and pivoting support 111 has one DOF, preferably rotations about axes substantially perpendicular to each other. A non-limiting example of such a pair of rotations is shown in FIGS. 4a and 4b, where joint mechanism 114 rotates about an axis parallel to second axis of rotation 141 and pivoting support 111 rotates about an axis of rotation perpendicular to this and parallel to the base of zoom mechanism 115. However, this embodiment is less preferred because of the possibility of pressure on the penetration point in a direction perpendicular to the third axis of rotation.

In preferred embodiments, one of pivoting support 111 and joint mechanism 114 is enabled to rotate about two substantially perpendicular axes of rotation, while the other joint mechanism rotates about a third axis of rotation, substantially perpendicular to both of the other axes of rotation. In some variants, pivoting support 111 can rotate about two substantially perpendicular axes of rotation, while joint mechanism 114 rotates about the third axis of rotation, substantially perpendicular to the other two, thereby enabling rotation of the endoscope about all three axes of rotation and preventing pressure on the penetration point. In other variants, joint mechanism 114 can rotate about two perpendicular axes of rotation, while pivoting support 111 rotates about the third axis of rotation, substantially perpendicular to the other two, thereby enabling rotation of the endoscope about all three axes of rotation and preventing pressure on the penetration point.

It should be further emphasized that while moving (rotating) the first mechanism (which comprises the first transmission means 101 and the second transmission means 102), the second mechanism (which comprises the third transmission means 103, the fourth transmission means 104 and the fifth transmission means 105) is moved (rotated) in the opposite direction and vice versa. Such reverse movement is highly important to compensate any unwanted/parasitic movement that would be created when moving only one mechanism.

Zoom mechanism 115 is connected to endoscope 200 and mechanically connected to pivoting support 111.

Reference is now made again to FIG. 4a which demonstrates in a non-limiting manner another object of the present invention.

In this figure is presented a mechanism forming a parallelogram for transferring rotational movement to the endoscope. As can be seen in the figure, the parallelogram comprises rod 172, adapted to transmit rotation around the second axis of rotation 141 to the endoscope, two rods 171 adapted to transmit rotation around the fifth axis of rotation 142, and rod 173 adapted to transmit motion of rods 171 and 172 to endoscope 200, wherein the two rods 171 are connected to rod 172 at one end and rod 173 at the other. Rods 171, 172 and 173 form a parallelogram.

Figure 5A:
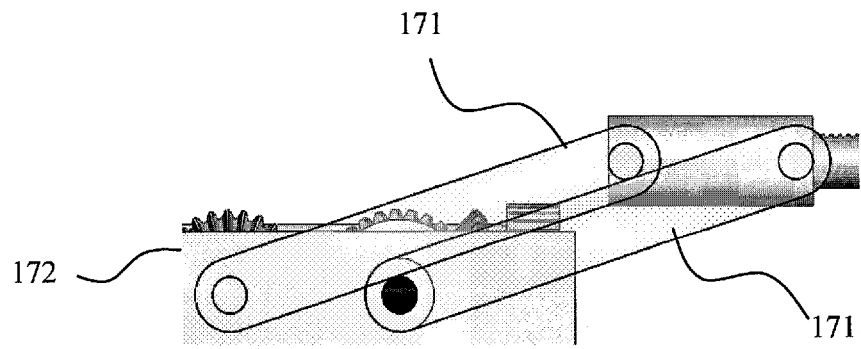
FIGS. 5a-b, 6a-c and 7a-b demonstrate more configurations of a maneuvering system unit for maneuvering an endoscope.
Figure 5B:
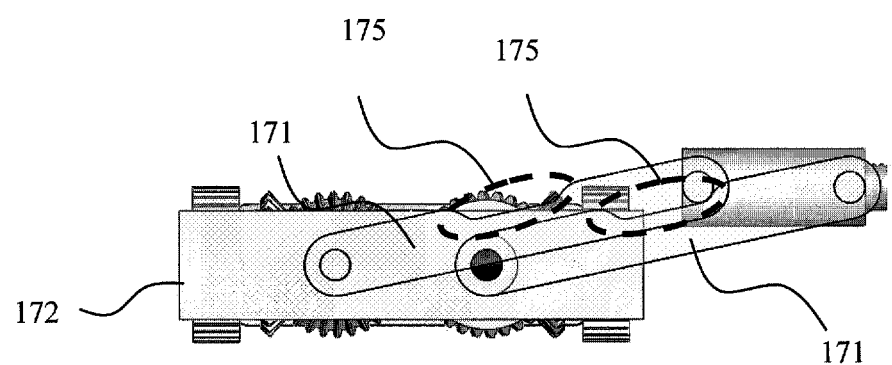

Reference is now made to FIGS. 5a and 5b, which illustrate in a non-limiting manner an embodiment of the parallelogram described above. FIG. 5a illustrates an embodiment in which ribs 171 have straight sides, while FIG. 5b illustrates an embodiment in which the ribs 171 comprise a dent (i.e., groove) 175.

FIG. 5a demonstrates the failure of rods 171 with straight sides to achieve a maximum 180 degree angle with respect to rod 172. This failure is the result of the collision between ribs 171.

In FIG. 5b a solution is suggested in a form of a dent 175 in rods 171 which enables a larger angular movement of ribs 171. By providing the dent (i.e., groove) 175, a greater angular extension is achievable.

Figure 6A:
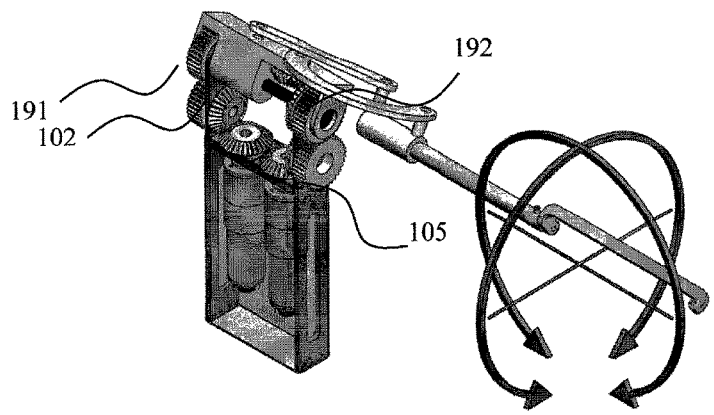
Figure 6B:
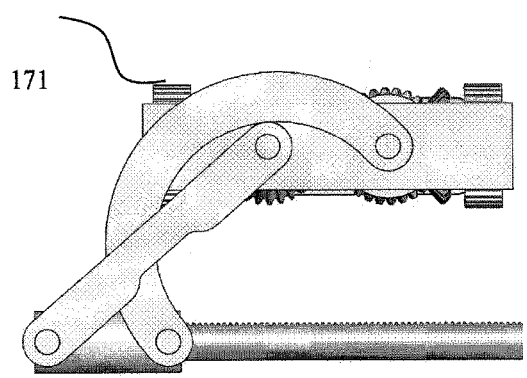
Figure 6C:
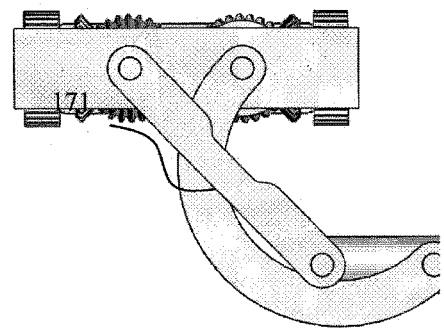

Reference is now made to FIGS. 6a, 6b and 6c, which illustrate in a non-limiting manner a parallelogram adapted to communicate between the different coaxial transmission means and the endoscope. In the figures, the above mentioned parallelogram is characterized by having at least one non-straight rib. As can be seen, at least one rib (171) is shaped like a circular arc.

According to the best embodiment of the present invention, the parallelogram with at least one arced side, an embodiment of which is illustrated in FIGS. 6a, 6b and 6c, provides the endoscope with a wider range of angular movements and maneuverability than a parallelogram with only straight sides. A comparison of the embodiment with straight sides shown in FIGS. 5a and 5b with the embodiment with an arced side shown in FIGS. 6a, 6b and 6c shows how this improved flexibility and maneuverability is achieved: the arc enables the rods 171 to move past each other and prevents them from colliding.

In addition, FIG. 6a describes two additional (and 'intermediate') coaxial means 191, 192 constructed upon second coaxial transmission means 102 and fifth coaxial transmission means 105, adapted to rotate the endoscope about two orthogonal axes.

It is within the best embodiment of the present invention to provide the first and second mechanisms having at least one first coaxial transmission means 101 (but it could be several interconnected transmissions); at least one second coaxial transmission means 102 (but it could be several communicating transmissions); at least one third coaxial transmission means 103 (but it could be several communicating transmissions); at least one second fourth transmission means 104 (but it could be several communicating transmissions); at least one fifth coaxial transmission means 105 (but it could be several communicating transmissions) and any combination thereof.

Figure 7A:
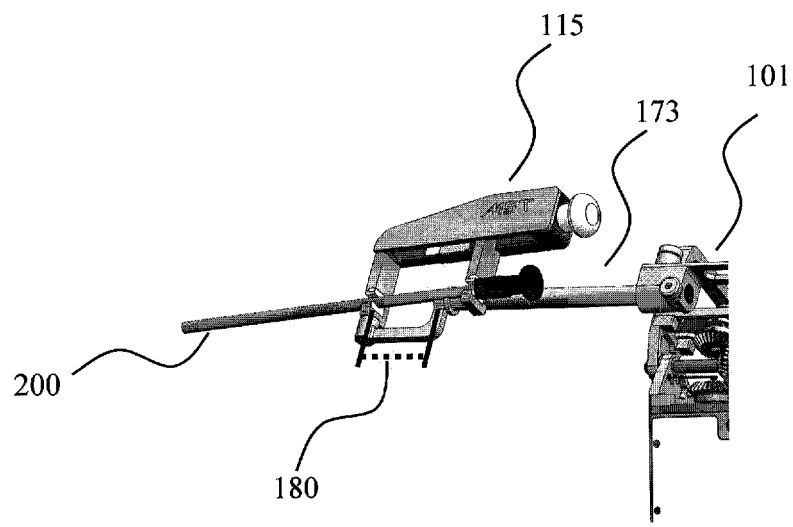
Figure 7B:
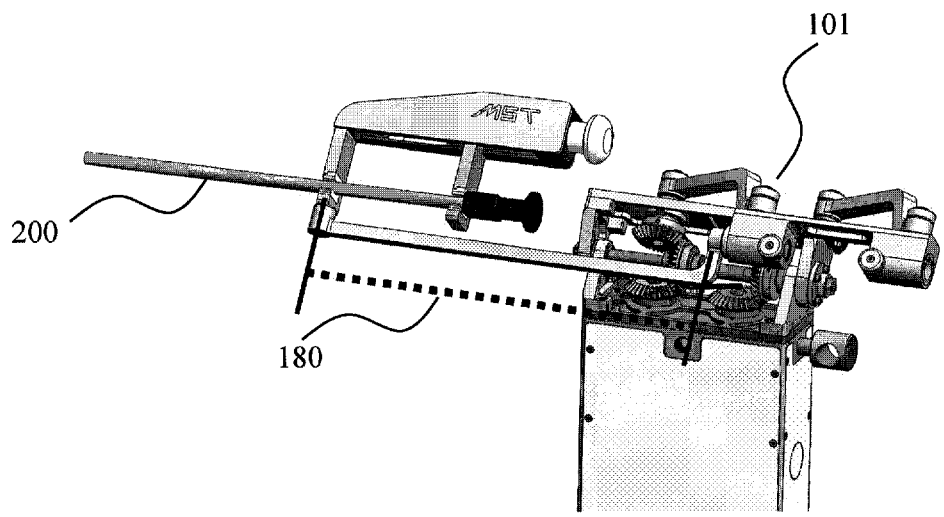

Reference is now made to FIGS. 7a and 7b, which illustrates in a non-limiting manner two different pre-determined distances 180.

FIG. 7a illustrates a relatively small predetermined distance 180, short enough that it limits the range of motion of the endoscope 200; FIG. 7b illustrates a larger predetermined distance 180, wherein the full range of motion of the endoscope 200 is enabled. In FIG. 7a, the predetermined distance 180 is small enough that, within the normal range of motion of zoom mechanism 115 and endoscope 200, the endoscope 200 or the zoom mechanism 115 are able to collide with rod 173 and/or first mechanism 101, whereas, as illustrated in FIG. 7b, the larger predetermined distance 180 is large enough that such collisions are impossible and the full range of motion of endoscope 200 is enabled.

In another embodiment of the present invention, maneuvering system 100 is characterized in a non-limiting manner by at least two configurations: an automatic configuration, in which system 100 is motorized; and a wholly manual configuration in which system 100 is maneuvered without mechanical assistance by a user of the system.

In the best embodiments, the SFME comprises switching means for reversibly switching from the manual configuration to the automatic configuration. The switching means can be manual or automatic. A non-limiting example of manual switching is the operator instructing the system, using any means known in the art, to begin automatic operation at the start of an operation. A non-limiting example of automatic switching is switching to manual operation in the event of a power failure. Manual switching means include, but are not limited to, switches, knobs, buttons and voice commands while automatic switching means include, but are not limited to, a response to a change in a sensor such as, for example, the loss of (or appearance of) the image of a human hand from a heat sensor or the loss of (or appearance of) the conductivity of a human hand from a conductivity sensor.

In another embodiment of the present invention, maneuvering system 100 comprises in a non-limiting manner a rotating means as described in FIG. 4a without pivoting support 111.

Figure 8:
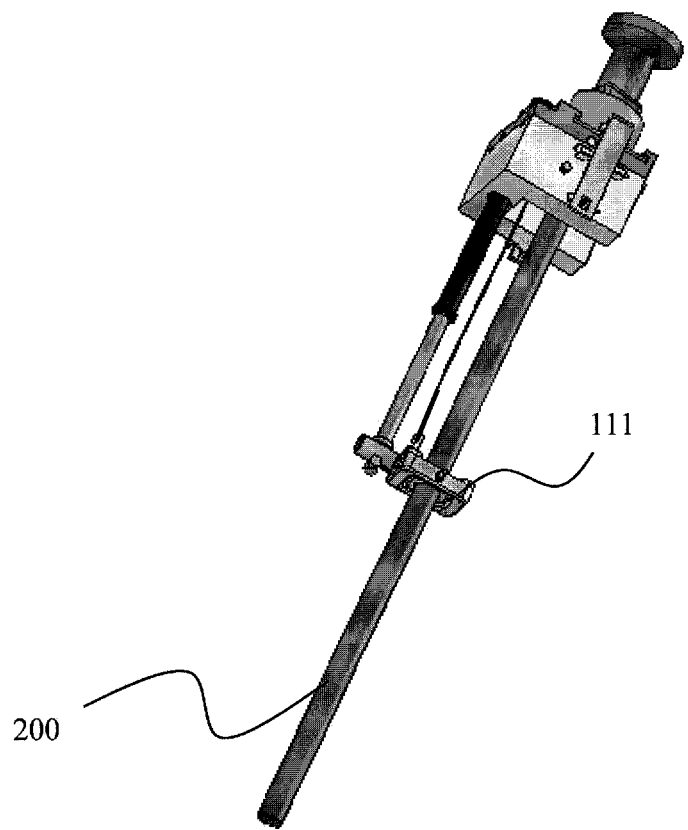
FIG. 8 presents an endoscope attached to a pivoting support.

Reference is now made to FIG. 8 which illustrates, in a non-limiting manner, pivoting support 111 as a gimbal coupled to endoscope 200.

Figures 9A, 9B:
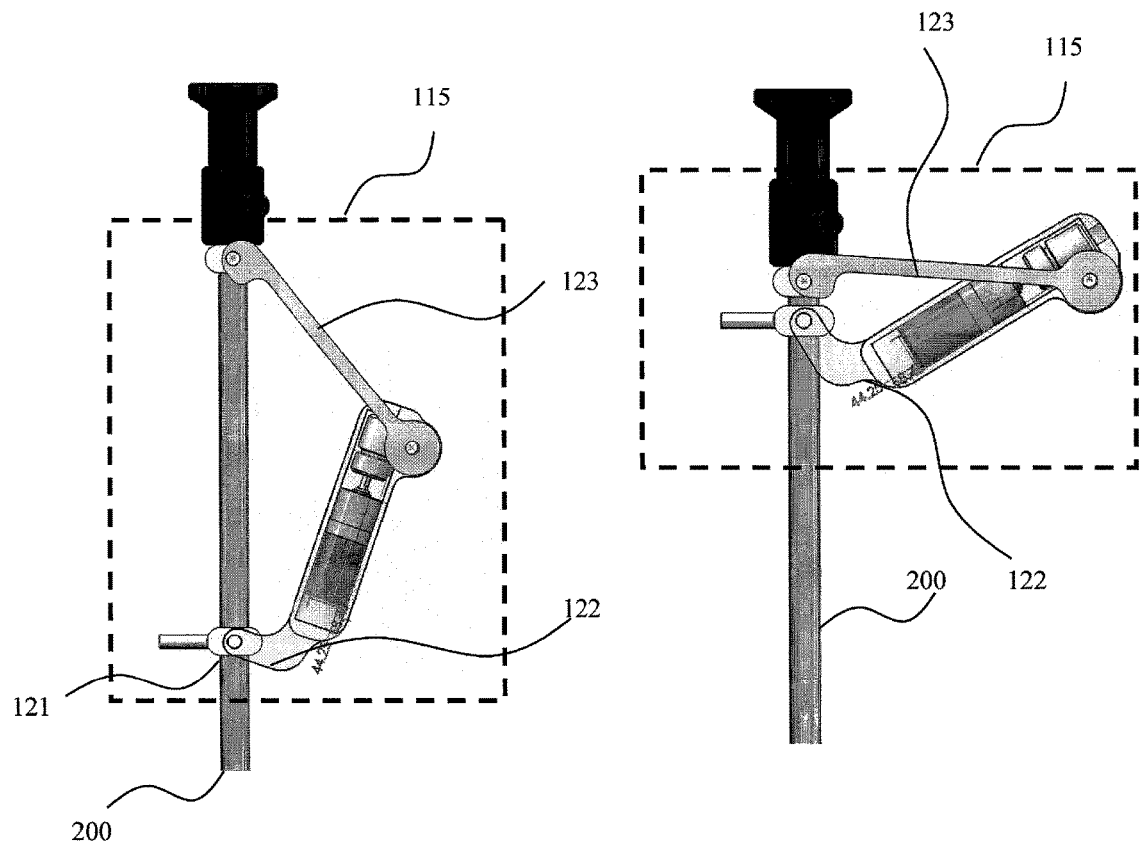
FIGS. 9a and 9b depict a zoom mechanism in two configurations.

FIGS. 9a-9b illustrate, in a non-limiting manner, one embodiment of a method whereby the zoom mechanism 115, which enables the endoscope 200 to translate along its main longitudinal axis, can be coupled to the pivoting support 111.

Reference is now made to FIG. 9a which illustrates a closer view of the zoom mechanism 115. According to this embodiment, the zoom mechanism 115 comprises (i) at least one first coupling means 121 slidably attached to endoscope 200; (ii) at least one first connecting means 122 reversibly coupled to endoscope 200 at a first coupling position; (iii) at least one second connecting means 123 reversibly coupled to first coupling means 122 at a second coupling position. Coupling between first connecting means 122, second connecting means 123 and endoscope 200 enables first connecting means 122 and second connecting means 123 to (i) pivot around the main longitudinal axis of endoscope 200; and, (ii) to move along the longitudinal axis of the endoscope 200.

Reference is now made to FIGS. 9a-9b which illustrate in a non-limiting manner, the zoom mechanism 115 as described above in two different positions of the first 122 and second 123 connecting means.

According to another embodiment of the current invention, zoom mechanism 115 comprises clasping means adapted to enable reversible reciprocating movement along the main longitudinal axis of endoscope 200.

In another embodiment of the current invention, first connecting means 122 and second connecting means 123 are connected to one another by means of a joint.

In another embodiment of the current invention, zoom mechanism 115 further comprises, in a non-limiting manner, m coupling means adapted to couple first connecting means 122 to second connecting means 123; where m is an integer greater than or equal to one.

In another embodiment of the current invention, m coupling means are rotatably coupled to each other.

In another embodiment of the current invention, coupling means are selected in a non-limiting manner from a group consisting, for example, of joints, rods, other zoom mechanisms and any combination thereof.

In another embodiment of the current invention, coupling of first connecting means 122 to endoscope 200 is obtained by means selected in a non-limiting manner from a group consisting, for example, of mechanical means, magnetic means and any combination thereof.

In another embodiment of the current invention, coupling of second connecting means 123 to endoscope 200 is obtained by means selected in a non-limiting manner from a group consisting, for example, of mechanical means, magnetic means and any combination thereof.

In another embodiment of the current invention, the mechanical coupling means are selected in a non-limiting manner from a group consisting, for example, of a clip, a fastening element, non-adhesive tape, adhesive tape, a snap fastener, a button and any combination thereof.

In another embodiment of the current invention, the magnetic coupling means comprises in a non-limiting manner at least one ferromagnet, at least one paramagnet and any combination thereof.

According to another embodiment of the present invention the zoom mechanism can be operated manually, automatically and any combination thereof.

According to another embodiment of the present invention the zoom mechanism can be operated by means of at least one motor.

In another embodiment of the current invention, third mechanism 112 additionally comprises in a non-limiting manner a plurality of q joints, at least one of which is coupled to pivoting support 111, and at least one of which is coupled to the second mechanism; where q is an integer greater than or equal to one.

In another embodiment of the current invention, third mechanism 112 without the gimbal also additionally comprises in a non-limiting manner a plurality of q joints, at least one of which is coupled to pivoting support 111, and at least one of which is coupled to the second mechanism; where q is an integer greater than or equal to one.

In another embodiment of the current invention, FCTM 101, SCTM 102, TCTM 103, FOCTM 104 and FTCTM 105 are selected in a non-limiting manner from a group consisting, for example, of gearwheels, wheels, crown gears, bevel gears, spur gears, belts, and any combination thereof.

In another embodiment of the current invention, the second plane defines in a non-limiting manner an angle $\theta$ and the fifth plane defines in a non-limiting manner an angle $\psi$. The angle $\theta$ varies between about 0 and about 360 degrees, preferably between about 0 and about 160 degrees. Additionally, the angle $\psi$ varies between about 0 and about 360 degrees, preferably between about 0 and about 140 degrees.

SFME 130 comprises a communication means and at least one joystick unit 152 coupled to endoscope 200, used to manually maneuver endoscope 200 in any direction defined by either one of $\psi$ and $\theta$ as defined above and in any combination thereof.

In another embodiment of the current invention, SFME 130 additionally comprises in a non-limiting manner means for controlling movement of endoscope 200, adapted to restrain the angular velocities of the endoscope in angular directions $\theta$ and $\psi$.

Figure 10:
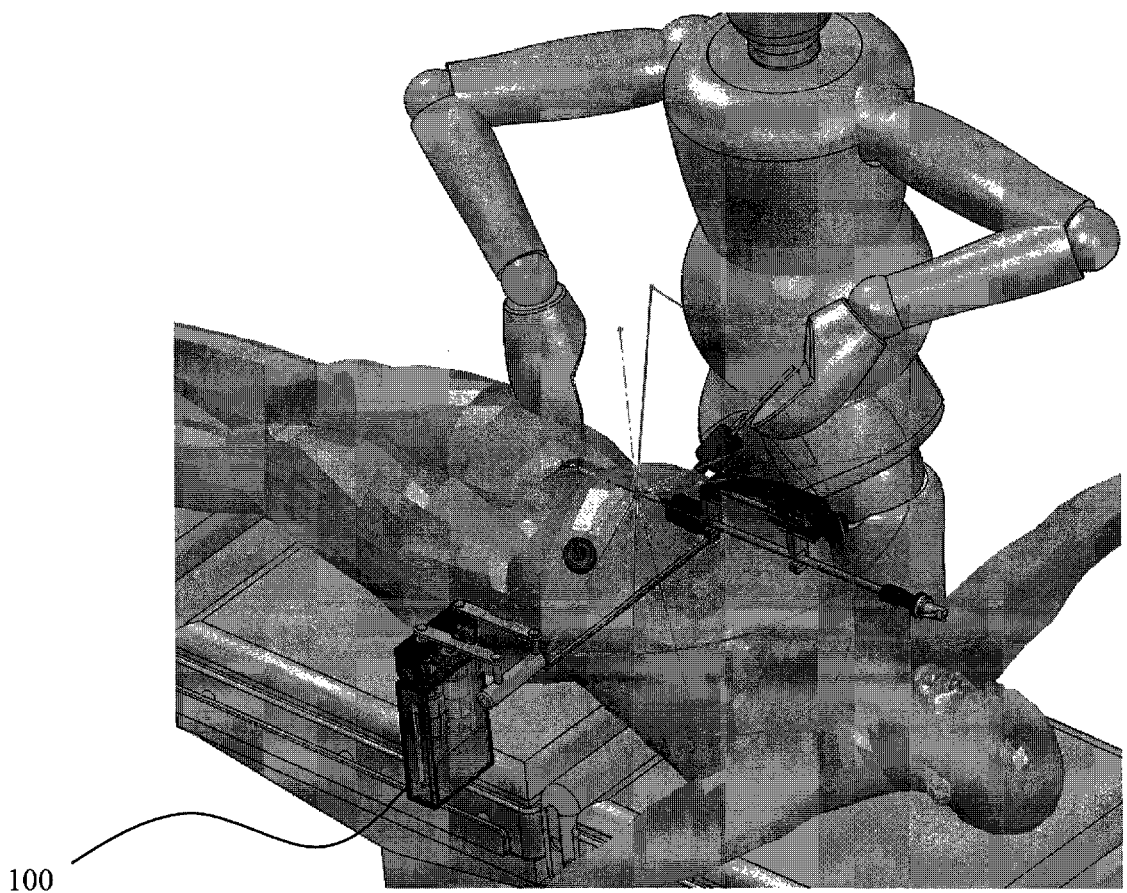
FIG. 10 presents a configuration of a maneuvering system unit with a hospital bed and an endoscope.

Reference is now made to FIG. 10, which presents, in a non-limiting manner, attaching means adapted to reversibly couple maneuvering system 100 to a hospital bed. Attaching means are selected in a non-limiting manner from a group consisting, for example, of mechanical means, magnetic means and any combination thereof. FIG. 10 also illustrates the best embodiment of the invention, which enables the utilization of the endoscope substantially tangential to the treated organ (e.g. the abdominal cavity).

The mechanical attaching means are selected in a non-limiting manner from a group consisting, for example, of a clip, a fastening element, adhesive tape, non-adhesive tape, a snap fastener, a button and any combination thereof.

The magnetic attaching means are selected in a non-limiting manner from a group consisting, for example, of a ferromagnet, a paramagnet and any combination thereof. The magnetic means is attached to one selected from a group consisting of a hospital bed, a maneuvering system, and any combination thereof.

In another embodiment of the current invention, maneuvering system 100 additionally comprises, in a non-limiting manner, a quick release handle adapted to disassemble endoscope 200 from maneuvering system 100.

In another embodiment of the current invention, the first mechanism additionally comprises, in a non-limiting manner, locking means adapted to maintain at least one selected from a group consisting, for example, of FCTM 101, SCTM 102 and any combination thereof in a predetermined orientation upon power failure; and to prevent any rotational movement of the same.

In another embodiment of the current invention, the second mechanism additionally comprises in a non-limiting manner locking means adapted to maintain at least one selected from a group consisting, for example, of TCTM 103, FOCTM 104, FTCTM 105 and any combination thereof in a predetermined orientation upon power failure; and to prevent any rotational movement of the same.

Figures 11A, 11B:
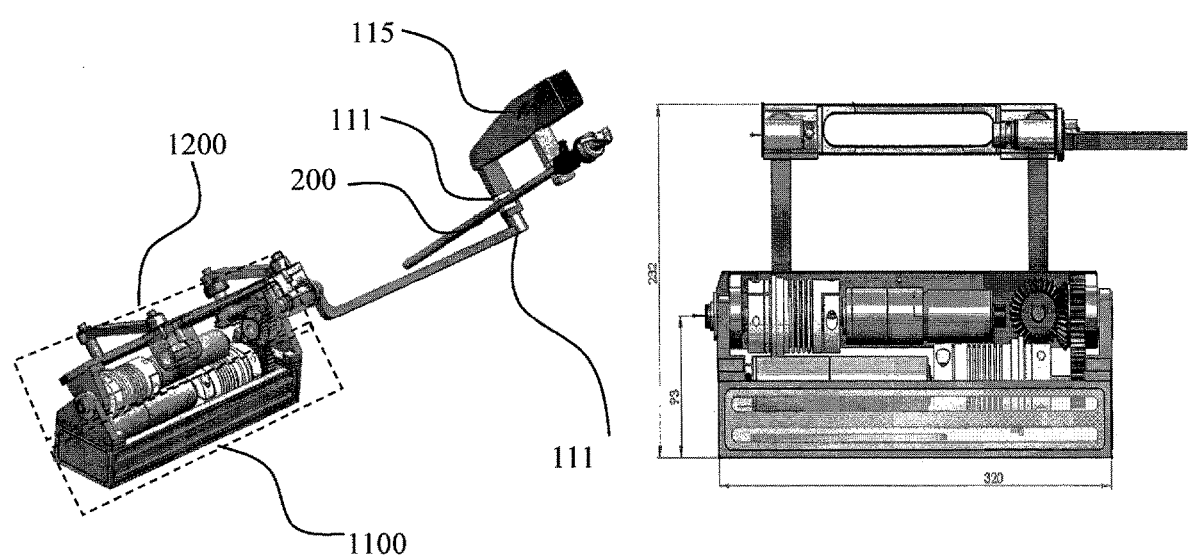

Reference is now made to FIGS. 11a and 11b both illustrating, in a non-limiting manner and from different points of view, first mechanism 1100 and second mechanism 1200 assembled in a horizontal configuration.

Reference is now made to FIGS. 12a and 12b both illustrating in a non-limiting manner different points of view of first mechanism 1100 and second mechanism 1200 assembled in a vertical configuration.

Reference is now made to FIGS. 13a and 13b both illustrating, in a non-limiting manner and from different points of view, first mechanism 1100 and second mechanism 1200 assembled in a compact vertical configuration.

Figure 14:
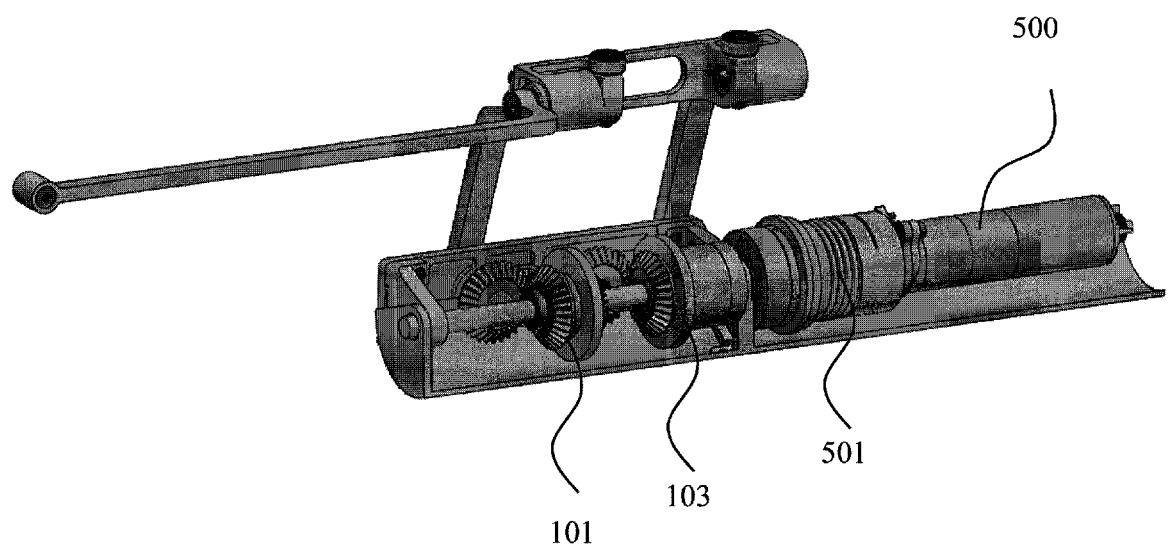

Reference is now made to FIG. 14 which depicts, in a non-limiting manner, one configuration of first mechanism 1100 and second mechanism 1200, where first rotation means 106 and second rotation means 107 (shown in FIG. 3) are unified to a single rotation means 500.

Said single rotation means 500 is provided with means adapted to switch between rotating first coaxial transmission means 101 and third coaxial transmission means 103 by a clutch 501.

In another embodiment of the current invention, the endoscope is adapted in a non-limiting manner to acquire real-time images of a surgical environment within a human body.

Figure 15:
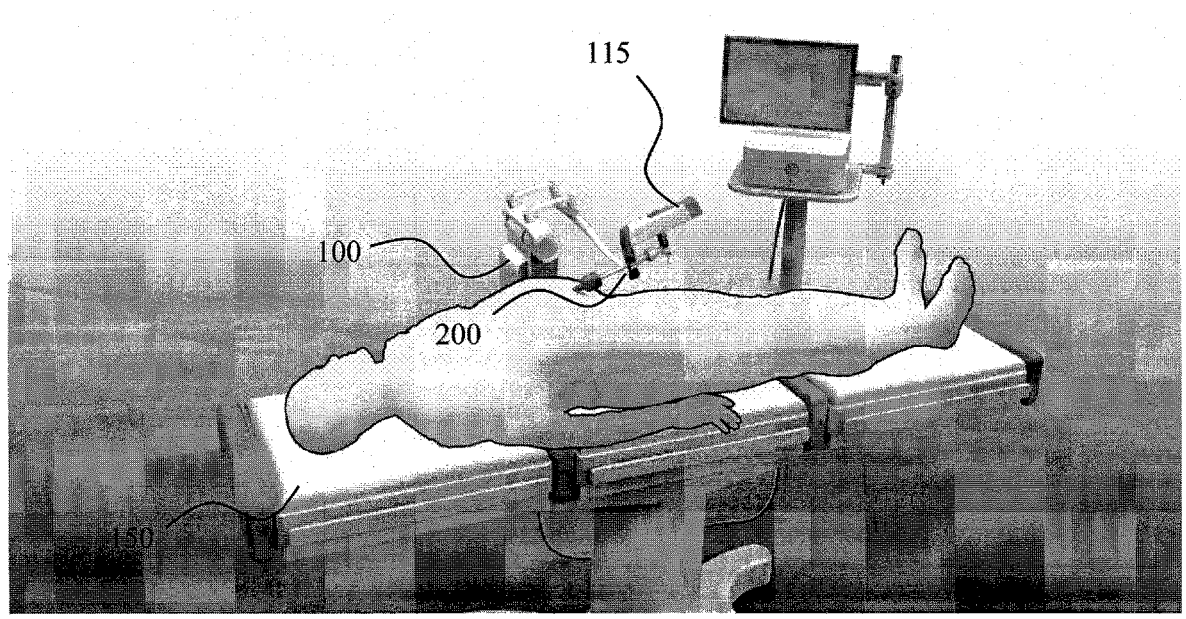
FIG. 15 shows an examining room configuration adapted to use a maneuvering system unit for maneuvering an endoscope.
Figure 16:
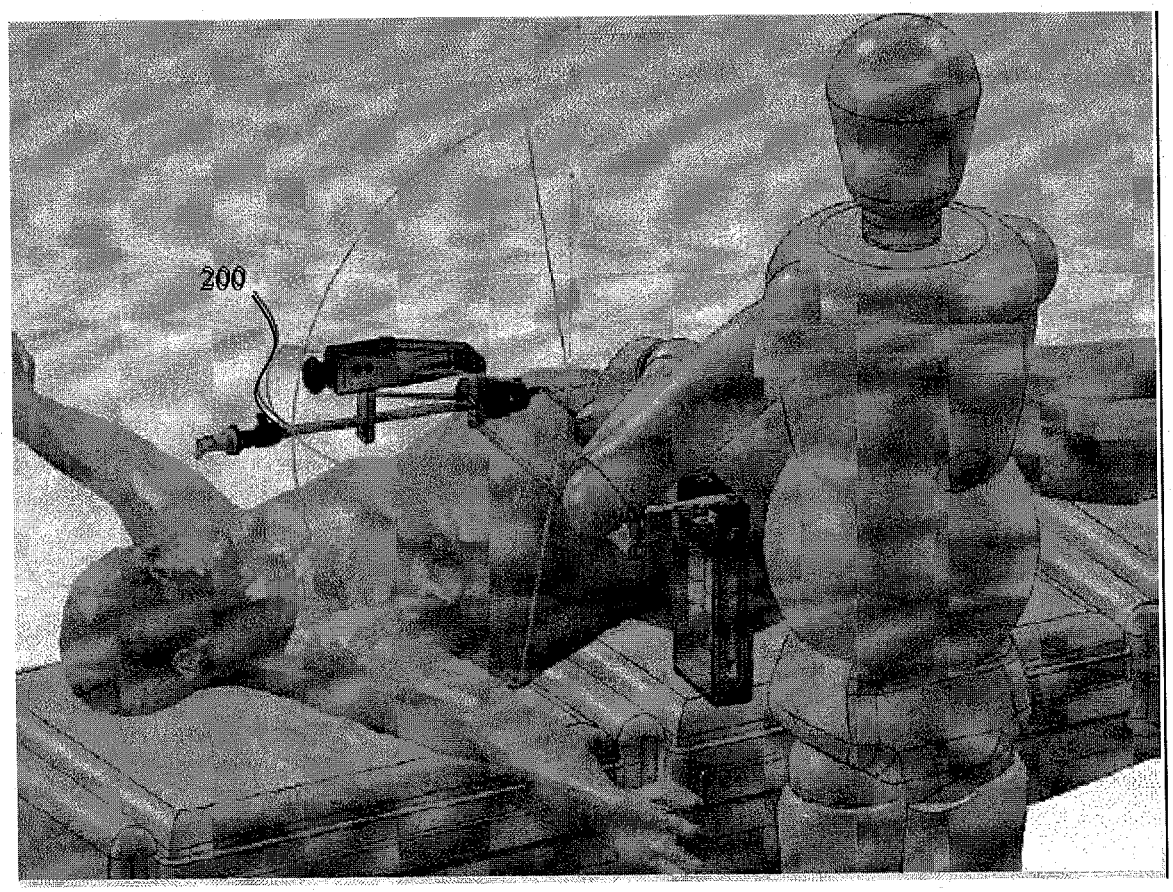
FIG. 16 depicts another configuration of a maneuvering system unit in an operating room with an emphasis on movement range.

Reference is now made to FIGS. 15 and 16 which present, in a non-limiting manner, possible configurations of the system, maneuvering system 100, endoscope 200, zoom mechanism 115, and hospital bed 150. As illustrated in FIG. 15, the system of the present invention enables the operation of the endoscope while the same is substantially perpendicular to the treated organ (e.g., the abdominal cavity) while FIG. 16 illustrates how the system of the present invention enables the operation of the endoscope while the same is substantially parallel to the treated organ (e.g., the abdominal cavity).

Reference is now made to FIG. 16 which presents in a non-limiting manner, a possible angle of the endoscope 200, in which the same is almost parallel to hospital bed 150.

Figure 17:
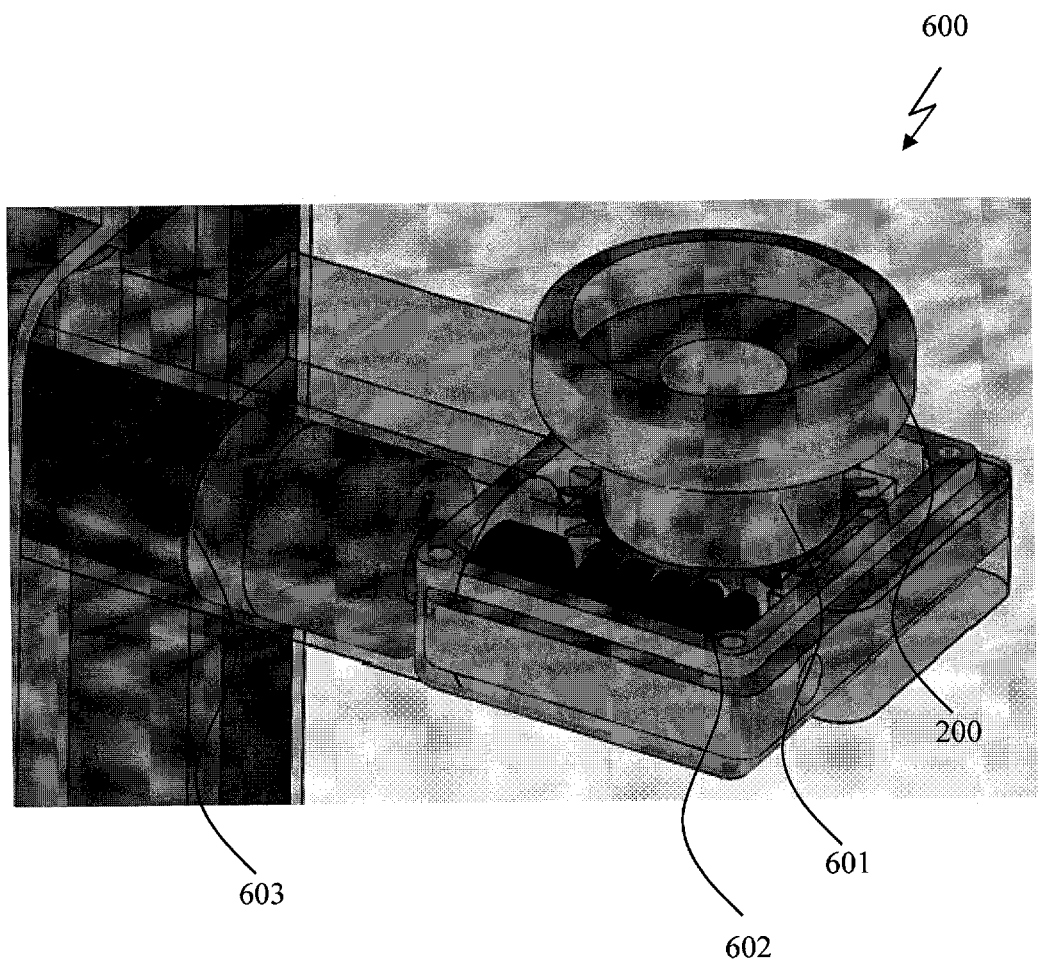
FIG. 17 presents a means adapted to rotate the endoscope around itself.
Figure 18:
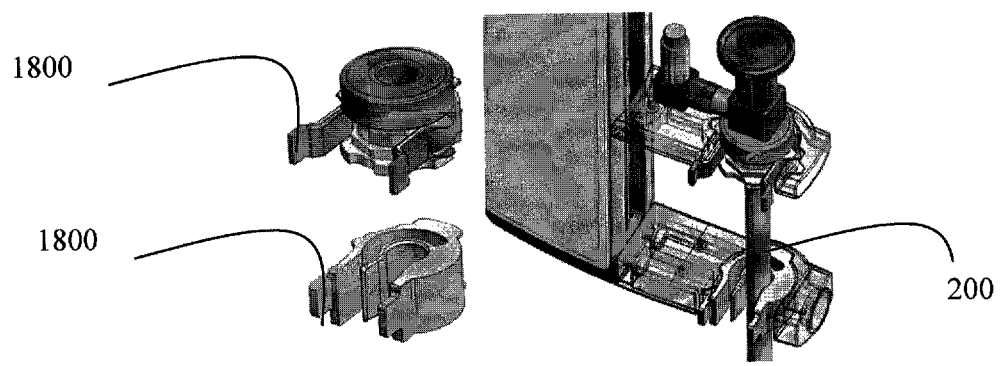
FIG. 18 presents another embodiment of the maneuvering system unit in which clips for enabling fast engagement and disengagement between the endoscope and the system are provided.
Figure 19:
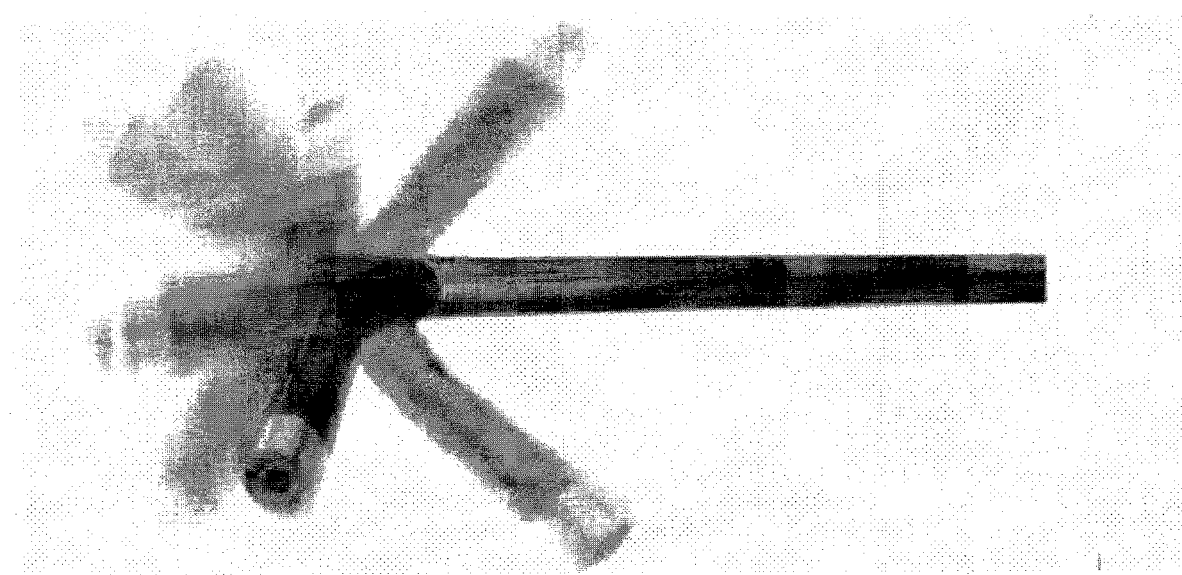
FIG. 19 illustrates an articulating endoscope.

Reference is now made to FIG. 17, which illustrates, in a non-limiting manner, means 600 adapted to rotate an endoscope around the endoscope's main longitudinal axis.

Means 600 comprises at least one transmission means 601 in communication with the endoscope 200; a second transmission means 602 in communication with first transmission means 601, and a motor 603 in communication with second transmission means 602, adapted to activate second transmission means 602.

Once the motor 603 is activated, second transmission means 602 is actuated and first transmission means 601 rotates. Once first transmission means 601 is activated, the endoscope is rotated around its main longitudinal axis.

According to another embodiment of the present invention, the SFME as described by any combination of the above embodiments may be employed on any non-human living being.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A system for maneuvering an endoscope (SFME) during a medical procedure, comprising:
    at least one maneuvering system, configured to maneuver said endoscope in at least two degrees of freedom (DOF), said maneuvering system comprising:
        at least one first pivoting support configured to be pivotally attached to said endoscope; said first pivoting support configured to enable said endoscope to pivot around an axis of rotation; and
        at least one second pivoting support in communication with said at least one first pivoting support, said second pivoting support configured to rotate around at least one axis being substantially orthogonal to said axis of rotation independently of said first pivoting support; thereby enabling said endoscope to rotate around an insertion point into a body of a subject in at least two orthogonal axes; and,
    at least one joystick in communication with said maneuvering system, configured to operate said maneuvering system;
    wherein operation of said joystick results in movement of said endoscope by means of said maneuvering system;
    wherein said endoscope is releasably attachable to said maneuvering system;
    further wherein magnitude of a velocity of said at least one joystick being above a predetermined value, magnitude of said velocity of said endoscope is no greater than a predetermined value;
    wherein said at least one maneuvering system comprises:
    a first mechanism, comprising:
        at least one first coaxial transmission; the first coaxial transmission defines a first plane and is characterized by a first axis of rotation which is substantially orthogonal to the first plane;
        at least one second coaxial transmission; the second coaxial transmission defines a second plane and is characterized by a second axis of rotation; the second axis of rotation is substantially orthogonal to the second plane; additionally, it is rotatably connected to the first coaxial transmission; where the second plane is substantially orthogonal to the first plane; and
        at least one first motor configured to rotate the first coaxial transmission around the first axis of rotation;
        where the first coaxial transmission transmits rotation to the second coaxial transmission; and,
    a second mechanism, comprising:
        at least one third coaxial transmission which defines a third plane and is characterized by a third axis of rotation; the third axis of rotation is substantially orthogonal to the third plane;
        at least one fourth coaxial transmission which defines a fourth plane and is characterized by a fourth axis of rotation, the fourth axis of rotation is substantially orthogonal to the fourth plane; and is rotatably connected to the third coaxial transmission; where the fourth plane is substantially orthogonal to the third plane;
        at least one fifth coaxial transmission which defines a fifth plane and a fifth axis of rotation; the fifth axis of rotation is substantially orthogonal to the fifth plane; fifth coaxial transmission is rotatably connected to the fourth coaxial transmission and is substantially orthogonal to the fourth plane;
        at least one second motor configured to rotate the third coaxial transmission around the third axis of rotation;
        where the third coaxial transmission transmits rotation to the fourth coaxial transmission; the fourth coaxial transmission transmits rotation to the fifth coaxial transmission;
        the first mechanism and the second mechanism are configured to rotate the endoscope around at least one second axis of rotation being substantially orthogonal to the second plane; and around at least one fifth axis of rotation being substantially orthogonal to the fifth plane, such that the second axis of rotation and the fifth axis of rotation are positioned at an angle A relative to each other; said angle A between said second axis of rotation and said fifth axis of rotation is in a range of about 0 degrees to about 180 degrees.

2. The system according to claim 1, wherein said at least one joystick is wearable by a user of said system.

3. The system according to claim 1, wherein said at least one joystick is coupled to at least one surgical tool used in said medical procedure.

4. The system according to claim 3, wherein said at least one surgical tool is said endoscope.

5. The system according to claim 1, wherein said movement of said joystick is proportional to said movement of said endoscope.

6. The system according to claim 1, wherein said joystick is a force joystick.

7. The system according to claim 1, wherein at least one of the following is true
   (a) said at least one joystick comprises a base and lever coupled to said base, such that movement of said lever results in movement of said endoscope; further wherein said movement of said lever is proportional to said movement of said endoscope;
   (b) said at least one joystick comprises a base and a button jointly connected to said base, such that movement of said button results in movement of said endoscope; further wherein said movement of said button is proportional to said movement of said endoscope;
   (c) said at least one joystick comprises a touchscreen, such that a touch and a movement on said touchscreen results in movement of said endoscope; further wherein said touch and movement on said touchscreen is proportional to said movement of said endoscope;
   (d) said at least one joystick comprises at least one sound sensor, configured to sense predetermined sound patterns; said joystick configured to operate said maneuvering system based on said predetermined sound patterns; and, any combination thereof.

8. The system according to claim 1, wherein said at least one joystick additionally comprises n sensors, where n is an integer larger than one; further wherein said sensors are selected from a group consisting of a motion sensor, a heat sensor, an electric sensor, a sound sensor, a pressure sensor, an optical sensor and any combination thereof.

9. The system according to claim 8, wherein at least one of the following is true
   (a) at least one of said n sensors is activated in case of power failure; and,
   (b) at least one of said n sensors is activated when said system is connected to power.

10. The system according to claim 1, wherein said at least one joystick is characterized by an external surface; further wherein said at least one motion sensor detects motion upon said external surface.

11. The system according to claim 8, wherein, at least one of the following is being held true (a) said at least one heat sensor is configured to sense temperatures in the range of about 35 degrees C. to about 42 degrees C.; said system being configured to enable maneuvering of said endoscope at such times as said at least one heat sensor senses temperatures in a range of about 35 degrees C. to about 42 degrees C. ; (b) said at least one heat sensor is configured to provide thermal image; said at least one heat sensor being coupled to a processing unit configured to provide said system user with said thermal image; said system being configured to enable maneuvering of said endoscope at such times as analysis of said thermal image by said processing unit detects the image of a human hand; said system being configured to prevent maneuvering of said endoscope at such times when said analysis of said thermal image by said processing unit fails to detect an image of a human hand; (c) said at least one electric sensor is configured to sense power failure; (d) said at least one electric sensor is configured to sense electric conductivity of a human body; further wherein said system is configured to enable maneuvering of said endoscope at such times when said sensor senses said electric conductivity of said human body; further wherein said system is adapted to prevent maneuvering of said endoscope at such times as said sensor fails to sense the conductivity of said human body; (e) said at least one sound sensor is configured to sense at least one predetermined sound pattern; further wherein said endoscope is maneuverable according to said at least one predetermined sound pattern sensed by said at least one sound sensor; (f) said at least one pressure sensor is configured to sense pressure applied to said at least one joystick; (g) said at least one optical sensor is configured to sense visual changes according to at least one predetermined visual pattern; further wherein said endoscope is maneuverable according to said at least one predetermined visual pattern; and any combination thereof.

12. The system according to claim 1, additionally comprising an interface system configured to enable communication between said at least one joystick and said maneuvering system; further wherein said interface system configured to enable communication comprises a member selected from a group consisting of a wired communication, a wireless communication and any combination thereof.

13. The system according to claim 1, wherein said at least one joystick is adapted to control and to direct said endoscope, via said maneuvering system, at a surgical tool.

* * * * *